(12) United States Patent
Yang et al.

(10) Patent No.: US 8,575,359 B2
(45) Date of Patent: Nov. 5, 2013

(54) ACID-SENSITIVE LINKERS FOR DRUG DELIVERY

(75) Inventors: Jerry Yang, La Jolla, CA (US); Seong Deok Kong, La Jolla, CA (US); Alice Luong, San Diego, CA (US); Stephen Howell, Del Mar, CA (US)

(73) Assignee: The Regents of the University of California, Oakland, CA (US)

( * ) Notice: Subject to any disclaimer, the term of this patent is extended or adjusted under 35 U.S.C. 154(b) by 733 days.

(21) Appl. No.: 12/295,858

(22) PCT Filed: Apr. 4, 2007

(86) PCT No.: PCT/US2007/008499
§ 371 (c)(1),
(2), (4) Date: Sep. 20, 2010

(87) PCT Pub. No.: WO2007/114946
PCT Pub. Date: Oct. 11, 2007

(65) Prior Publication Data
US 2011/0053878 A1 Mar. 3, 2011

Related U.S. Application Data

(60) Provisional application No. 60/789,014, filed on Apr. 4, 2006.

(51) Int. Cl.
| | |
|---|---|
| *C07D 233/00* | (2006.01) |
| *C07D 233/02* | (2006.01) |
| *C07D 233/54* | (2006.01) |
| *C07D 233/60* | (2006.01) |
| *C07H 15/24* | (2006.01) |

(52) U.S. Cl.
USPC .................. 548/300.1; 548/341.5; 536/6.4

(58) Field of Classification Search
USPC ............................. 536/6.4; 548/300.1, 341.5
See application file for complete search history.

(56) References Cited

U.S. PATENT DOCUMENTS 4,246,021 A 1/1981 Gilmour et al.

OTHER PUBLICATIONS

Tang et al., J. Am. Chem. Soc., 1978, 100, 3918-3922.*
Matevosyan et al., Zhurnal Obshchei Khimii ,1980, 50(7), 1506, English abstract, retreived on Nov. 15, 2012 from STN database, 1 pages.*
Kong et al., Bioconjugate Chem., 2007, 18, 293-296.*
Ota., Englsih abstract of JP 03101664, retrieved from STN database on Feb. 25, 2013, 1 page.*
Curtis, N. J. et al., "An easily introduced and removed protecting group for imidazole nitrogen: a convenient route to 2-substituted imidazoles", Journal of Organic Chemistry 45:4038-4040, 1980.
International Preliminary Report on Patentability and Written Opinion dated Oct. 8, 2008 for International Application No. PCT/US2007/08499, 5 pages.
International Search Report dated May 7, 2008 for International Application No. PCT/US2007/08499, 1 page.
Patel, Vinod F. et al., "Novel acid labile COLI trityl-linked difluoronucleoside immunoconjugates: synthesis, characterization, and biological activity", Bioconjugate Chemistry 7:497-510, 1996.

* cited by examiner

*Primary Examiner* — Eric S Olson
*Assistant Examiner* — Zhengfu Wang
(74) *Attorney, Agent, or Firm* — Kilpatrick Townsend & Stockton LLP

(57) ABSTRACT

The invention is in general directed to acid-sensitive linkers, and methods of use thereof, such as, for example, in drug delivery methods.

6 Claims, 6 Drawing Sheets

1 R = R' = H
2 R = Br, R' = H
3 R = NO₂, R' = H
4 R = Butyl, R' = H
5 R = H, R' = Br
6 R = H, R' = OMe
7 R = H, R' = CN
8 R = H, R' = NO₂

ACID-SENSITIVE LINKERS FOR DRUG DELIVERY

PRIORITY

Priority is claimed to U.S. Provisional Application Ser. No. US 60/789,014, filed Apr. 4, 2006, and entitled "New pH-Sensitive Linkers for Drug Delivery," which is referred to and incorporated herein by reference in its entirety.

FIELD OF THE INVENTION

The invention is in general directed to acid-sensitive linkers, and methods of use thereof, such as, for example, in drug delivery methods.

BACKGROUND

Chemotherapy has made a significant impact on the longevity and quality of life of those affected by cancer. The influence a drug may have on the outcome of cancer treatments, however, is highly dependent on the ability of the therapeutic to selectively and effectively kill targeted malignant cells while leaving normal cells untouched. Addressing this challenge has been a central focus for the discovery of new therapeutics that can alter specific biological processes that are critical to the survival of cancer cells. New methods of administering drugs (i.e., orally, systemically, or loco-regionally) also plays a critical role in the development of new treatment strategies for effective management of cancer. [10-16] Although a number of small molecules are known to have potent cytotoxicity towards cancer cells, relatively few anticancer agents are used clinically due, in part, to low therapeutic windows for drug efficacy compared to drug-related toxicity.[17] Drug delivery systems (DDSs) have, therefore, attracted wide attention in cancer research due to their potential to significantly reduce the toxicity of anticancer agents in normal healthy tissues, while making it possible to control the concentration and location of active drugs released in the body over long periods of time.[18] DDSs may also be used to increase the potency of drugs by increasing their accumulation at targeted tissues compared to administration of equitoxic levels of free drugs in solution.[19, 20]

DDSs have already been shown to play a critical role in the development of effective therapeutic strategies against several forms of cancer.[21] Nanoparticle carriers, for instance, are useful as systemically-administered delivery vessels for cancer therapeutics to solid tumors[22-26] due to their enhanced permeability from leaky blood vessels in tumor tissues compared to blood vessels in healthy tissues.[27-29]

An important issue in determining the effectiveness of a DDS is the ability to control the location and time over which active drug release occurs. This challenge has motivated the development of methods to trigger the release drug loads from DDSs upon arrival at the target site. The use of heat [37], light [38], or ultrasonic radiation [39, 40], for example, has been reported to trigger the release of encapsulated drugs from DDSs. Although these triggering methods show promise for the treatment of some forms of cancer, the requirement of external stimuli to catalyze the local release of drugs may limit these therapeutic approaches to certain areas of the body (e.g., the extremities). Another valuable approach for triggering the release of therapeutics from DDSs for the treatment of cancer could be to exploit differences in the natural physiological environment of tumors compared to normal tissues. Differences in acidity, for instance, are particularly interesting as a stimulus to distinguish between normal and malignant tissues since it is well documented that the extracellular pH of many tumors is slightly more acidic than the blood or normal tissues.[31, 41-43] In addition, the endocytosis of polymers and nanoparticles by tumor cells has also been observed;[44] endocytosis is expected to deliver DDSs to endosomes and lysosomes, the pH of which is 2 orders of magnitude lower than plasma pH.

Among the many challenges in engineering effective cancer drug delivery systems is the development of simple methods to incorporate large loads of therapeutic agents to the delivery vessels that are released in active form primarily at the targeted site. Previously reported delivery vessels, mostly polymer-based, are often designed to display the controlled release of active agents via dissolution, matrix degradation, diffusion, or cleavage of covalently-attached prodrugs.[21] Organic functional groups that decompose slowly in an aqueous environment have attracted wide interest as potential linkers for the covalent conjugation of drugs to polymers for a range of drug delivery applications. [43, 45-50]

Recent findings suggest that a promising strategy for developing effective DDSs is to covalently attach therapeutics to delivery vessels via acid-sensitive linkers.[20, 30, 31] The improved in vivo efficacy for the treatment of solid tumors using acid-sensitive linkers in polymer-based drug delivery systems compared to administration of free drug in solution encourages the development of new general methods to exploit acid-catalyzed activation to control the release of a broad spectrum of potent cytotoxic agents from polymeric DDSs. Drug delivery systems have also included the encapsulation of drugs non-covalently in carriers that are preferentially released in an acidic environment. An ethyoxyethyl protecting group for imidazoles was shown to be hydrolytically unstable in aqueous acidic conditions at elevated temperatures. [69]

Other linking systems explored by researchers include, for example, the covalent conjugation of drugs via linkers that are cleaved by disease specific enzymes, or linkers that are sensitive to oxygen levels.

New strategies for preparing DDSs that are capable of retaining high loads of cancer therapeutics and selectively releasing them in a targeted tissue will help ameliorate many of the current problems in chemotherapy.

Although several acid-sensitive linkers have been reported for conjugation of certain classes of small molecule cytotoxic agents to polymers,[45-50] there is a need for linker systems that have the advantages of: 1) facile attachment of a broad range of cytotoxic agents to drug delivery carriers; 2) tunable rates of cleavage under mild aqueous acidic conditions for exploring optimal rates of drug release for, for example, cancer therapy; and 3) adaptability for conjugating drugs to a range of drug delivery carriers. These advantages will provide a means to rapidly synthesize a range of e.g., polymeric drug delivery systems carrying a variety of therapeutic agents that can be release from the polymers at controlled rates in a tumor-specific environment. The utility of acid-sensitive linkers is not limited to the delivery of drugs for cancer treatment. Other areas where tunable acid-sensitive linkers may be useful include therapeutics for non-cancerous conditions, and the delivery of compounds other than therapeutics, such as, for example, imaging agents.

SUMMARY

The invention is in general directed to acid-sensitive molecules that hydrolyze with tunable rates under physiological conditions, and methods of use thereof. The acid-sensitive molecules of the present invention may be used, for example, in drug delivery systems. Such DDSs may comprise, for example, a drug delivery vessel, an acid-sensitive linker, and a therapeutic. Such DDS may also comprise, for example, a delivery vessel, and acid-sensitive linker, and a non-therapeutic compound, such as, for example, an imaging agent.

Functional groups that decompose in acidic environments, for instance, may be useful for the development of cancer drug delivery systems where an acid-sensitive group could exploit the lower extracellular pH (for example, pH 5.5, between about pH 5 and 7, between about pH 5 and 6, between about pH 5.2 and 5.8, between about 5.5 and 6, between about 6 and 6.9, between about 6.2 and 6.8, or between about 6.4-6.9) of some tumor cells, compared to that of blood or normal tissues, to trigger the release of therapeutic agents from suitable delivery vessels.

Functional groups that cleave under mild acid may also exploit the low pH of endosomes (pH about 5.5-6) and lysosomes (pH about 4.5-5) to trigger the release of covalently linked therapeutics from drug delivery carriers after endocytosis by targeted cells. (20, 31, 75)

DETAILED DESCRIPTION

Figure 1:
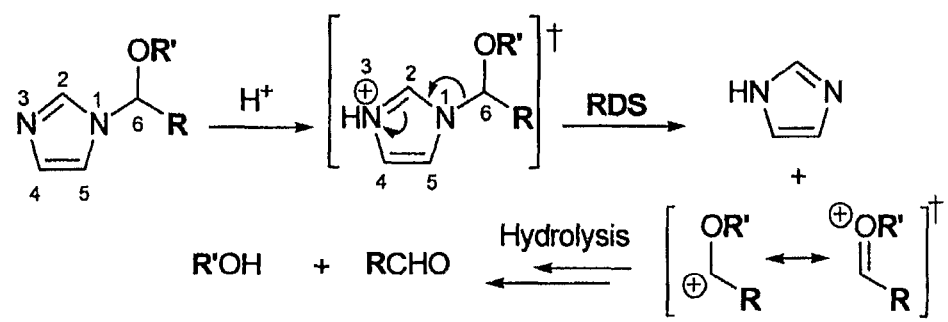
FIG. 1 depicts a proposed mechanism for the hydrolysis of N-alkoxyalkylimidazoles in aqueous acidic solutions. RDS=rate determining step.
Figure 2:
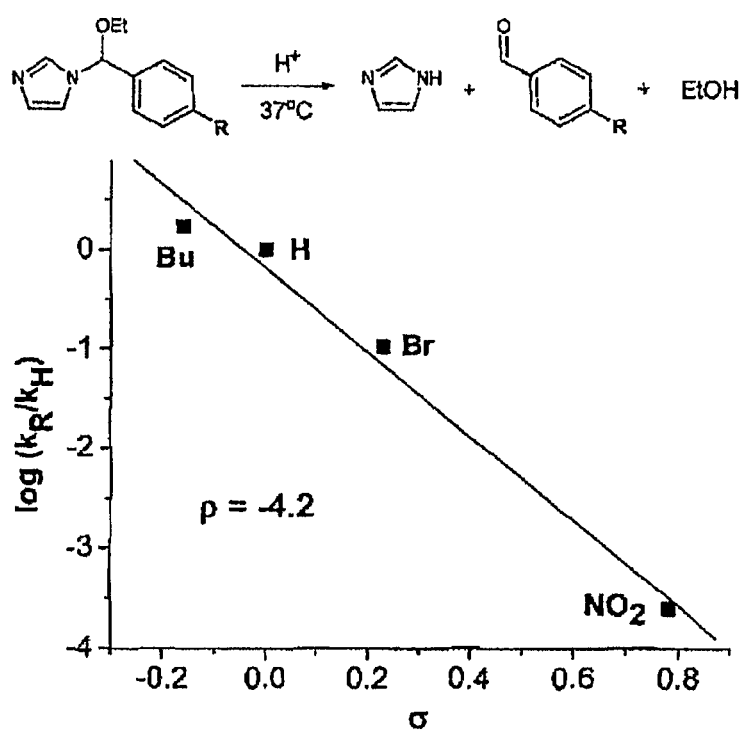
FIG. 2 depicts a linear Hammett correlation for the hydrolysis of compounds 1-4 in 0.5 M MES buffered $D_2O$ (pD=5.5) at 37° C., where R=n-butyl (Bu), H, Br, and $NO_2$.

It has been found that N-linked imidazoles may be used as tunable acid-sensitive linkers. These linkers undergo hydrolysis in aqueous acidic solutions at physiological temperature, upon protonation of the imidazole group. The difference in the protonated state of certain N-linked imidazoles in acidic pH environments (for example, pH 5.5) compared to normal, physiological pH (for example pH 7.4; pKa of imidazolium ions have been reported to be between 5 and 7 (Bruice, T. C., and Schmir, G. L., J. Am. Chem. Soc. 1958, 80:148-156)) this difference may be useful for initiating the rapid release of molecules, for example drugs, linked to imidazole-containing delivery vessels when exposed to tumor-like environments.

Thus, in a first embodiment of the invention is a compound having the formula

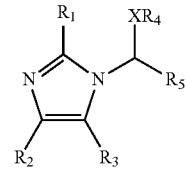

wherein $R_1$ is selected from the group consisting of H, Br, $NO_2$, Butyl, OMe, CN, methyl, carboxy, methyl carboxylate, a drug delivery vessel, a therapeutic, and an imaging agent;

$R_2$ is selected from the group consisting of H, $NO_2$, Butyl, OMe, CN, Histidine, histamine, a drug delivery vessel, a therapeutic, and an imaging agent;

$R_3$ is selected from the group consisting of H, $NO_2$, Butyl, OMe, CN, a drug delivery vessel, a therapeutic, and an imaging agent, or one of $R_2$ and $R_3$ is selected from the group consisting of Br, 2-aminoethyl, acetate, and N-(prop-2-ynyl)acetamide and one of $R_2$ and $R_3$ is H;

$R_4$ is selected from the group consisting of $OCH_2CH_3$ and $OCH_3$ $R_5$ is selected from the group consisting of methyl, H, and

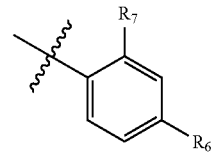

$R_6$ is selected from the group consisting of H, an electron withdrawing group, an electron donating group, $COR_8$, $COR_9$, a drug delivery vessel, a therapeutic, and an imaging agent;

$R_7$ is selected from the group consisting of H, an electron withdrawing group, an electron donating group, $COR_8$, $COR_9$, a drug delivery vessel, a therapeutic, and an imaging agent;

$R_8$ is a hydroxyl-containing therapeutic or imaging agent;

$R_9$ is an amine-containing therapeutic or imaging agent; and

X is selected from the group consisting of C, O, N, S, and P.

In certain embodiments, $R_6$ is selected from the group consisting of H, Br, $NO_2$, Butyl; $COR_8$, $COR_9$, a drug delivery vessel, a therapeutic, and an imaging agent. In certain embodiments, $R_7$ is selected from the group consisting of H, Br, OMe, CN, $NO_2$, $COR_8$, $COR_9$, a drug delivery vessel, a therapeutic, and an imaging agent. In certain exemplary embodiments, $XR_4$ is OEt. In some aspects of the invention, $R_1$, $R_2$, and $R_3$ are H. In some aspects of the invention, $R_6$ is $COR_8$, $COR_9$, a therapeutic, or an imaging agent.

In some aspects of the invention, at least one of the therapeutics is a cancer therapeutic. In some aspects, the therapeutic is selected from the group consisting of therapeutics 1, 3, or 5. Where therapeutics are covalently attached to the linkers of the present invention, it is to be understood that the therapeutic attached may actually be a derivative, with modifications at the linking site.

In some embodiments, $R_6$ is selected from the group consisting of CO-Doxorubicin, and CO-Strophanthidin. In other aspects, $R_7$ is selected from the group consisting of CO-Doxorubicin, and CO-Strophanthidin. In some aspects, $R_5$ is selected from the group consisting of therapeutic derivative 2, 4, or 6.

Also exemplified in the present invention, are compounds that can be used as linkers wherein therapeutics, drug delivery vessels, and imaging agents may be covalently attached using chemical synthesis processes known to those of ordinary skill in the art. In some examples, $R_1$ is selected from the group consisting of H, Br, $NO_2$, Butyl, OMe, CN, methyl, carboxy, and methyl carboxylate; $R_2$ is selected from the group consisting of H, $NO_2$, Butyl, OMe, and CN; $R_3$ is selected from the group consisting of H, $NO_2$, Butyl, OMe, and CN or one of $R_2$ and $R_3$ is selected from the group consisting of Br, 2-aminoethyl, acetate, and N-(prop-2-ynyl)acetamide and one of $R_2$ and $R_3$ is H; $R_6$ is selected from the group consisting of an electron withdrawing group, and an electron donating group; and $R_7$ is selected from the group consisting of an electron withdrawing group, and an electron donating group. In certain embodiments, $R_6$ is selected from the group consisting of H, Br, and $NO_2$, and Butyl and $R_7$ is selected from the group consisting of H, Br, OMe, CN, and $NO_2$.

In certain embodiments of the invention, the compound is insoluble at pH 7.4 and may be hydrolyzed at pH 5.5. In some aspects, the compound hydrolyzes about 10 times faster at pH 5.5 than at pH 7.4.

In some aspects of the invention, the compound is selected from the group consisting of compounds 1, 2, 3, 4, 5, 6, 7, 8, 9, and 10.

Also provided are methods of synthesizing an acid-sensitive linker modified therapeutic or imaging agent, comprising the steps of obtaining a compound of the present invention and covalently binding said compound, or a derivative thereof, to a therapeutic or imaging agent. In certain aspects, the compound is covalently bound to a therapeutic. In some exemplary aspects, the therapeutic is a cancer therapeutic. In certain aspects, the compound is covalently bound to an imaging agent.

Also provided are drug delivery systems comprising a compound of the present invention. The drug delivery systems may, for example, have a structure T-X-V, wherein T is a delivery vessel, V is a therapeutic, and X is a compound of the present invention. It is understood by those of ordinary skill in the art that one, two, or all three of T, X, and V may actually be derivatives in that there may be modifications to the chemical structure at the attachment site.

In some embodiments of the present invention are provided acid-sensitive linkers comprising a compound of the present invention. In some aspects, a method is provided of synthesizing an acid sensitive linker, comprising the steps of FIG. 3.

Also provided in the present invention are transdermal patches for administering a compound of the present invention.

In other embodiments, a compound is provided, having the formula

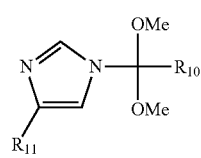

wherein
$R_{10}$ is selected from the group consisting of H, an electron withdrawing group, an electron donating group, $COR_8$, $COR_9$, a drug delivery vessel, a therapeutic, and an imaging agent
$R_{11}$ is selected from the group consisting of H, an electron withdrawing group, an electron donating group, $COR_8$, $COR_9$, a drug delivery vessel, a therapeutic, and an imaging agent;
$R_8$ is a hydroxyl-containing therapeutic or imaging agent; and
$R_9$ is an amine-containing therapeutic or imaging agent.

In some aspects, $R_{10}$ is selected from the group consisting of H, Me, and phenyl, and $R_{11}$ is selected from the group consisting of H and Br. In some aspects, the compound is selected from the group consisting of WW, XX, YY, and ZZ.

Also provided are methods of administering a therapeutic or imaging agent to an individual, comprising administering a compound of the present invention, in a therapeutically effective amount.

In other exemplary embodiments are provided a method of inhibiting cell proliferation, comprising contacting said cells with therapeutic 5 or therapeutic derivative 6. Also provided is a method of inhibiting the growth of cancer cells comprising contacting said cells with therapeutic 5 or therapeutic derivative 6.

By "acid-sensitive linker" is meant that the linker undergoes hydrolysis in the presence of acid. The linker may be, for example, pH sensitive, or the linker may undergo hydrolysis in the presence, for example, of a Lewis acid.

In some aspects of the invention, the compound, or linker, is pH-sensitive. By "pH-sensitive" is meant that the linker undergoes hydrolysis at certain pH levels and not others, or that the linker undergoes measurably quicker hydrolysis at certain pH levels and not others. In some examples, more hydrolysis is observed when the linker is in lower pH conditions than when the linker is in higher pH conditions. For example, a linker may undergo accelerated hydrolysis at pH ranging between 5 and 6.5, compared to at a pH ranging between 7 and 7.5. By "tunable" or adjustable, is meant that the conditions under which the linker undergoes hydrolysis may be adjusted based on modifications that may be made to the molecule. Examples of modifications include, for example, modifications to R groups or other substituents of the imidazole, such as, for example, those discussed herein.

The hydrolytic properties of acid sensitive N-linked imidazoles may be exploited for use as acid-sensitive linkers in cancer drug delivery systems. Drug delivery systems, including cancer drug delivery systems, may be used to exploit the lower extracellular pH (for example, pH 5.5) of some tumor cells [1] compared to that of blood or normal tissues, to trigger the release of therapeutic agents from a drug carrier. [2-9] The simple structure of the acid sensitive N-linked imidazoles of the present invention makes it possible to covalently attach a broad range of small molecule therapeutics to e.g., polymeric drug delivery carriers that can take advantage of the numerous pH gradients that exist in normal and diseased cells for targeted delivery of drugs.

By "electron donating group" is meant electron donating groups appropriate for drug design known to those of ordinary skill in the art, as, for example, presented herein, and as presented in Corwin Hansch, A. Leo, and R. W. Taft, Chem. Rev. 1991, 91:165 "A survey of Hammett substituent constants and resonance and field parameters"

By "electron withdrawing group" is meant electron withdrawing groups appropriate for drug design known to those of ordinary skill in the art, as, for example, presented herein, and as presented in Corwin Hansch, A. Leo, and R. W. Taft, Chem.

Rev. 1991, 91:165. The methods of the present invention may be used to deliver imaging agents to tissues or bodily fluids. For example, an acid-sensitive linker of the present invention may be linked to an imaging agent. This may, for example, assist in directing the imaging reagent to its intracellular or extracellular target. Imaging agents are known to those of ordinary skill in the art, and include, for example, substances administered to illuminate a physiological function within a patient, while leaving other physiological functions generally unaffected, such as, for example, imaging agents containing radioisotopes such as indium or technetium; contrasting agents containing iodine or gadolinium; enzymes such as horse radish peroxidase, GFP, alkaline phosphatase, or .beta.-galactosidase; fluorescent substances such as europium derivatives; luminescent substances such as N-methylacrydium derivatives, proton relaxation agents, and fluorescent chromophores.

The cleavage of ethoxyethyl groups on imidazoles involves the protonation of the imidazole nitrogen (N3) followed by the breaking of the C6-N1 bond as the rate-determining step (FIG. 1). These molecules can be used to conjugate a range of therapeutic agents (FIG. 1, R, or R') to imidazole-containing drug delivery vessels for controlled release of therapeutics in a mild acidic environment. The mild conditions required to synthesize the N-ethoxybenzylimidazoles (FIG. 3) should provide for a simple route to incorporate this functionality into imidazole-containing delivery vessels. The ability to tune the rates of hydrolysis of the N-ethoxybenzylimidazoles may make it possible to optimize the rate of release of drugs attached to delivery vessels via these acid sensitive functionalities for maximal efficacy for e.g., cancer therapy.

In some aspects of the invention are provided methods of synthesis of N-ethoxybenzylimidazoles. These methods include, for example, the use of simple and mild conditions that are amenable to conjugating a range of therapeutic agents to drug delivery vessels using these linkers.

In other aspects of the invention are provided methods of tuning acid-sensitive linker molecules. These methods allow the controlled release of drugs from suitable delivery vessels. In other aspects of the invention are provided tunable linker molecules.

Also provided in the present invention are methods of linking a range of drug containing amine or alcohol groups at various positions on an acid-sensitive linker. Also provided are sets of acid-sensitive linker molecules comprising amine or alcohol groups covalently linked at various positions on the molecules. Classes of compounds, such as, for example therapeutic agents and imaging agents, include, for example, small molecules, peptides, and nucleic acids. Examples of therapeutics that may be used, for example, in the treatment of cancer, non-cancer therapeutics, and imaging agents, that may be used in the methods of the present invention include, but are not limited to—organic small molecules: including all hydroxyl and amine containing therapeutics for the treatment of cancer, for example, molecules that inhibit the replication of DNA (e.g., Doxorubicin, Epirubicin, Calecheamicin, Camptothecin), molecules that stabilize or disrupt microtubules (e.g., Paclitaxel, Docetaxel, Epothilone), molecules that affect the Na$^+$/K$^+$ pump (e.g., Strophanthidin), molecules that affect the function of the Golgi apparatus (e.g., Norrisolide and active derivatives of Norrisolide); —inorganic small molecules: including all hydroxyl and amine containing therapeutics for the treatment of cancer, for example, cisplatin or oxoplatin; peptides, proteins, and nucleic acids, including, for example, silencing RNA, antisense compounds, gene therapeutics. Examples of linked anti-tumor agents include, for example, CO-Doxorubicin, and CO-Strophanthidin.

Further examples of therapeutics and imaging agents include, but are not limited to proteins: including proteins of human and non-human origin, for example, antibodies (e.g. trastuzumab), hormones (e.g. leutinizing hormone, follicle stimulating hormone), cytokines (e.g. IL-6), growth factors (e.g. G-CSF), bacterial or plant toxins (e.g., *Pseudomanas* toxin, gelonin, ricin, abrin) and tumor-targeting soluble proteins of any type; peptides: including engineered and natural peptides that are toxic to tumor cells, that alter the architecture or function of such cells, or target other molecules to tumor cells or cells in the tumor that serve to support tumor cells, for example, Lysins, TAT-related proteins that enhance cell penetration; RNA, for example, anti-sense RNA, toxin aptamers; DNA: including naturally-occurring and synthetic oligonucleotides and higher molecular weight structures, for example, plasmid and viral vectors that express RNAs or proteins that are toxic to tumor cells; particles: including polymer-derived, protein-derived, metal-derived and inorganic-based particles of any size, for example, nanoparticles loaded with therapeutic drugs, imaging agents or radionuclides; small molecules: including both inorganic and organic small molecules that target cell surface receptors or otherwise bind to the surface or other accessible intracellular or extracellular components of tumor cells, or that bind to other cellular or matrix components of a tumor, for example, all hydroxyl and amine containing therapeutics for the treatment of cancer, cancer chemotherapeutic agents that inhibit DNA, RNA or protein synthesis (e.g. doxorubicin, epirubicin, calecheamicin, camptothecin, 5-fluorouracil), form adducts in DNA or RNA: (e.g., cisplatin, oxaliplatin, carboplatin, melphalan), stabilize or disrupt microtubules (e.g., paclitaxel, docetaxel, epothilone), molecules that affect the Na+/K+ pump (e.g., Strophanthidin), molecules that affect the function of the Golgi apparatus (e.g., Norrisolide and active derivatives of Norrisolide), molecules that disrupt angiogenesis such as antibodies to VEGF (bevacizumab), recombinantly produced molecules that function to mimic receptors (VEGF trap) or integrins, metals that can serve as contrast agents (e.g. gadolinium, technetium, iron, iodine), and molecules that are themselves radionuclides or contain or chelate radionuclides such as iodine, yttrium, strontium.

Examples of drug delivery vessels, or carriers, that may be used in the present invention, include, for example, polymers, including polymers based on polysaccharaides, polypeptides, 2-hydroxypropylmethylacrylamide (HPMA), polylactic acid, polyglycolic acid, and other biocompatible polymers; proteins, including proteins of human and non-human origin, for example, antibodies (e.g. trastuzumab), human serum albumin (HSA), hormones (e.g. leutinizing hormone, follicle stimulating hormone), cytokines (e.g. IL-6), growth factors (e.g. G-CSF) and tumor-targeting soluble proteins of any type; peptides, including engineered and natural peptides that target cell surface receptors or otherwise bind to the surface of tumor cells, or that bind to other cellular or matrix components of a tumor, for example, stomatostatin, gonadotropin releasing factor, LyP-1, CREKA; RNA, including, for example, RNA aptamers, including those designed for intraocular administration; DNA: including naturally-occurring and synthetic oligonucleotides and higher molecular weight structures, for example, gene therapy vectors; particles, including polymer-derived, protein-derived, metal-derived and inorganic-based particles of any size, including, for example, nanoparticles, examples include human serum albumin particles containing (Abraxane) (Fe containing contrast agent); small molecules, including both inorganic and organic small molecules that target cell surface receptors (e.g., folic acid) or otherwise bind to the surface or other accessible intracellular or extracellular components of tumor cells, or that bind to other cellular or matrix components of a tumor, for example, folic acid, leucovorin, biotin. Other drug delivery vessels or carriers include, for example, creams, ointments, adhesives, medication delivery patches, foams, aerosols, and other vehicles used for the delivery of therapeutic or imaging agents. etc.

Also provided in the present invention are drug delivery systems, comprising a drug delivery vessel, a therapeutic drug molecule, and an acid-sensitive linker. The drug delivery vessel, may be, for example, a molecule that targets particular tissues, a polymer, a peptide, or other such molecule that otherwise affects the uptake of the therapeutic drug molecule. The acid-sensitive linker may be, for example, tunable. The therapeutic drug molecule, or therapeutic, may be, for example, a cancer therapeutic. Also provided in the present invention are methods of treating cancer comprising administering a drug delivery system of the present invention.

Also provided in the present invention are transdermal patches comprising the linked compounds of the present invention. Tunable linkers may be used as part of transdermal patches for drug delivery.

Compounds and Formulation

While the compositions and methods of the present invention will typically be used in therapy for human patients, they may also be used in veterinary medicine to treat similar or identical diseases. The compositions may, for example, be used to treat mammals, including, but not limited to, primates and domesticated mammals. The compositions may, for example be used to treat herbivores. The compositions of the present invention include geometric and optical isomers. The compositions and methods of the present invention may also be used to deliver compounds in a controlled release manner to plants. In some embodiments, the compound may be delivered to the plants, for example, by spraying the plants, in order to obtain controlled release of a compound, such as, for example, a treatment for plant cancer, an insecticide, or a growth enhancer.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

The compounds of the present invention may exist as pharmaceutically acceptable salts. The present invention includes such salts. The term "pharmaceutically acceptable salts" is meant to include salts of active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids, for example, acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Compounds of the present invention may also be in the form of pharmaceutically acceptable esters. The pharmaceutically acceptable esters in the present invention refer to nontoxic esters, preferably the alkyl esters such as methyl, ethyl, propyl, isopropyl, butyl, isobutyl or pentyl esters, of which the methyl ester is preferred. However, other esters such as phenyl-C.sub.1-5 alkyl may be employed if desired. Ester derivatives of the described compounds may act as prodrugs which, when absorbed into the bloodstream of a warm-blooded animal, may cleave in such a manner as to release the drug form and permit the drug to afford improved therapeutic efficacy.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium (3H), iodine-125 ($^{125}$I) or carbon-14 ($^{14}$C). All isotopic variations of the compounds of the present invention, whether radioactive or not, are encompassed within the scope of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" in reference to a particular disease includes prevention of the disease.

A compound of the present invention can be formulated as a pharmaceutical composition. Such a composition can then be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches or iontophoresis devices. The term parenteral as used herein includes subcutaneous injections, intravenous, intramuscular, intrasternal injection, or infusion techniques. Formulation of drugs is discussed in, for example, Hoover, John E., Remington's Pharmaceutical Sciences, Mack Publishing Co., Easton, Pa.; 1975. Other examples of drug formulations can be found in Liberman, H. A. and Lachman, L., Eds., Pharmaceutical Dosage Forms, Marcel Decker, New York, N.Y., 1980.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Suppositories for rectal administration of the drug can be prepared by mixing the drug with a suitable nonirritating excipient such as cocoa butter, synthetic mono- di- or triglycerides, fatty acids and polyethylene glycols that are sold at ordinary temperatures but liquid at the rectal temperature and will therefore melt in the rectum and release the drug.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, a contemplated aromatic sulfone hydroximate inhibitor compound can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. A contemplated aromatic sulfone hydroximate inhibitor compound can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form varies depending upon the mammalian host treated and the particular mode of administration.

Kits

The present invention further provides kits comprising linker molecules, and may further comprise compositions or components that may be used to prepare drug delivery systems. For example, such kits may comprise acid-sensitive, tunable, linker molecule of the present invention. Such kits may further comprise a delivery vessel, or at least one delivery vessel, such as, for example, a polymer, or such kits may further provide compositions or components used for covalently attaching a linker molecule to a therapeutic. Such kits may further comprise a therapeutic, or at least one therapeutic, such as, for example, an antitumor agent, or such kits may further provide compositions or components used for covalently attaching a linker molecule to a drug delivery carrier. Kits may also include instructions for attaching the linker molecule to a delivery vessel, such as, for example, a polymer, or to a therapeutic.

EXAMPLES

The following examples demonstrate, for example, that N-ethoxybenzylimidazoles hydrolyze in aqueous solutions at physiological temperatures with hydrolysis occurring approximately 10 times faster in acidic solutions compared to solutions at normal, physiological pH. By incorporating electron donating or electron withdrawing substituents, the rates of hydrolysis of the N-linked imidazoles in mild acidic solutions may be tuned. This tuning may be accomplished, for example, by modifications to the linker or incorporating different R groups. For example, using these modifications, the linkers may be cleaved within the timeframes of 30 seconds, to 30 minutes, to 3-4 months, to more than 9 months.

Example 1

General Procedure for the Synthesis of N-ethoxybenzylimidazoles

All reagents were purchased from Sigma-Aldrich, Inc., TCI, or Alfa Aesar and used without further purification. Doxorubicin (AKA Adriamycin) was from Bedford Laboratories. NMR spectra were recorded on a Varian 400(FT, 400 MHz, $^1$H; 100 MHz, $^{13}$C) spectrometer. HRMS (high-resolution mass spectra) were obtained in the Department of Chemistry & Biochemistry, University of California, San Diego. Kinetic analysis by reverse-phase high performance liquid chromatography (RP-HPLC) was performed with an Agilent 1100 Series HPLC using an analytical reverse-phase column (SPHERI-5 Phenyl 5 micron, 250×4.6 mm).

A solution of benzaldehyde (6.82 mmol), triethyl orthoformate (3.3 g, 22.5 mmol), and conc. HCl (10 μL, 90 μmol) was refluxed in 3.7 mL of ethanol for 24 hrs. Diethyl ether was added and the organic layer was extracted with 3×2 M NaOH. The organic layer was dried over anhydrous $Na_2SO_4$. After removal of diethyl ether under reduced pressure, the crude mixture was distilled under vacuum (55-65° C./0.5 mmHg) to give pure benzaldehyde diethylacetal (82-91% yield). All acetals were characterized by $^1$H-NMR and used without further purification.

A mixture of imidazole (1.0 g, 14.7 mmol), benzaldehyde diethylacetal (58.8 mmol), and p-toluenesulfonic acid (84 mg, 0.441 mmol) was heated neat at 110° C. for 1-3 days, accompanied by concurrent distillation of ethanol. After cooling, sodium carbonate (0.47 g, 4.41 mmol) was added and the crude mixture was distilled under vacuum (150-170° C./0.5 mmHg) to give N-ethoxybenzylimidazole derivatives (1-8) (15-75% yield).

Example 2

Hydrolysis of N-ethoxybenzylimidazole

Mechanistically, the cleavage of ethoxyethyl groups on imidazoles had been proposed to involve the protonation of the imidazole nitrogen (N3 in FIG. 1) followed by the breaking of the C6-N1 bond as the rate determining step (RDS, FIG. 1). To attain a related N-linked imidazole that could undergo acid hydrolysis at physiological temperatures, substitution of the ethyl group (i.e., bearing the C6 carbon in FIG. 1) with benzyl groups was tested to determine if it would lower the activation energy-required for this hydrolysis reaction and facilitate the cleavage of the C6-N1 bond under physiological conditions.

Figure 3:
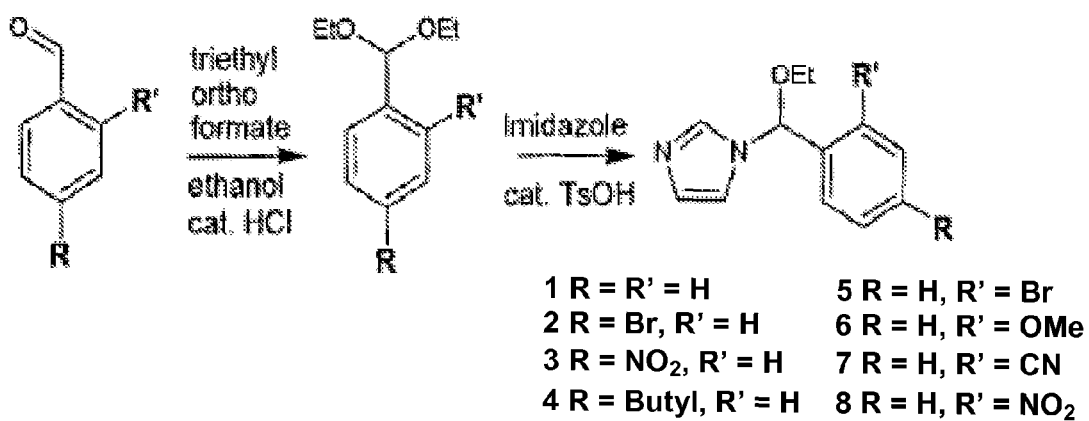
FIG. 3 depicts an example of a general procedure for the synthesis of N-ethoxybenzylimidazoles 1-8 from the corresponding benzaldehydes.

N-ethoxybenzylimidazole 4 was synthesized from benzaldehyde using a simple and mild two step procedure (FIG. 3, Example 1).

At 37° C. in 0.5 M HEPES buffer in $D_2O$ (pD=7.4), $^1$H-NMR analysis determined that 1 hydrolyzes with a half-life of 25 hours to give imidazole, ethanol, and benzaldehyde as the only products detected. (FIG. 1). For all hydrolysis studies in $D_2O$, 20-40% $d_6$ DMSO (v/v) was added to improve the solubility of the molecules. The addition of 20-40% DMSO did not affect the pH of the solutions or the rate of hydrolysis of 1. At 37° C. in 0.5 M MES buffer in $D_2O$ (pD=5.5), 1 hydrolyzed to give the same products as at higher pD (FIG. 1) but with a much shorter half-life of 1.7 hours for hydrolysis. Kinetic analysis indicated that the hydrolysis of 1 is first-order dependent on the concentration of 1 and zero-order dependent on the concentration of buffering agent.[53] As expected from the proposed mechanism shown in FIG. 1, the benzyl group (R=Phenyl) appears to stabilize the transition state of the rate determining step better than the previously reported[69] ethyl group (R=Methyl) and, thus, facilitates hydrolysis of 1 at physiological temperatures. The pKa of the protonated form of 5 (as a representative N-ethoxybenzylimidazole) was measured to be 5.4 (The pKa of 5 was measured in 50:50 $H_2O$:DMSO by titration of 5 with a concentrated solution of HCl. The pKa of 5 was estimated by measuring the pH of the solution when half an equivalent of HCl was added), the observed acceleration of the rate of hydrolysis of 1 in mild acidic solution compared to physiological pH is also consistent with the proposed mechanism (FIG. 1).

Characterization of 1: $^1$H NMR (CDCl$_3$, 400 MHz) δ 1.258 (t, 3H), 3.539 (m, 2H), 6.178 (s, 1H), 6.955 (s, 1H), 7.078 (s, 1H), 7.290-7.327 (m, 5H), 7.673 (s, 1H); $^{13}$C NMR (CDCl$_3$, 100 MHz) δ 14.839, 64.469, 86.854, 116.970, 125.654, 128.357, 128.766, 129.647, 136.249, 137.616; HRMS (m/z) calcd for $C_{12}H_{14}N_2O$ (M$^+$), 202.1101; found, 202.1102.

Characterization of 2: $^1$H NMR (CDCl$_3$, 400 MHz) δ 1.254 (t, 3H), 3.523 (m, 2H), 6.136 (s, 1H), 6.920 (s, 1H), 7.091 (s, 1H), 7.177 (d, 2H), 7.474 (d, 2H), 7.673 (s, 1H); $^{13}$C NMR (CDCl$_3$, 100 MHz) δ 14.954, 64.686, 86.308, 116.948, 123.043, 127.563, 130.088, 131.631, 136.398, 136.885; HRMS (m/z) calcd for $C_{12}H_{13}BrN_2O$ (M$^+$), 280.0206; found, 280.0207.

Characterization of 3: $^1$H NMR (CDCl$_3$, 400 MHz) δ 1.297 (t, 3H), 3.573 (m, 2H), 6.268 (s, 1H), 6.927 (s, 1H), 7.132 (s, 1H), 7.506 (d, 2H), 7.724 (s, 1H), 8.217 (d, 2H); $^{13}$C NMR (CDCl$_3$, 100 MHz) δ 14.979, 65.019, 85.813, 116.881, 123.804, 127.031, 130.682, 136.535, 144.476, 148.155; HRMS (m/z) calcd for $C_{12}H_{13}N_3O_3$ (M$^+$), 247.0951; found, 247.0954.

Characterization of 4: $^1$H NMR (CDCl$_3$, 400 MHz) δ 0.902 (t, 3H), 1.260 (t, 3H), 1.322 (m, 2H), 1.562 (m, 2H), 2.588 (t, 2H), 3.547 (m, 2H), 6.162 (s, 1H), 6.974 (s, 1H), 7.085 (s, 1H), 7.157 (d, 2H), 7.211 (d, 2H), 7.677 (s, 1H); $^{13}$C NMR (CDCl$_3$, 100 MHz) δ 13.998, 14.882, 22.346, 33.539, 35.324, 64.428, 86.955, 116.981, 125.596, 128.392, 129.707, 135.003, 136.274, 143.633; HRMS (m/z) calcd for $C_{16}H_{22}N_2O$ (M$^+$), 258.1727; found, 258.1728.

Characterization of 5: $^1$H NMR (CDCl$_3$, 400 MHz) δ 1.258 (t, 3H), 3.583 (m, 2H), 6.417 (s, 1H), 6.959 (s, 1H), 7.049 (s, 1H), 7.218 (t, 1H), 7.370 (t, 1H), 7.536 (d, 1H), 7.645 (d, 1H), 7.701 (s, 1H); $^{13}$C NMR (CDCl$_3$, 100 MHz) δ 14.874, 64.754, 85.960, 116.979, 122.396, 127.356, 127.605, 129.400, 130.410, 132.916, 136.490, 136.632; HRMS (m/z) calcd for $C_{12}H_{13}BrN_2O$ (M$^+$), 280.0206; found, 280.0203.

Characterization of 6: $^1$H NMR (CDCl$_3$, 400 MHz) δ 1.253 (t, 3H), 3.549 (m, 2H), 3.747 (s, 1H), 6.472 (s, 1H), 6.841 (d, 1H), 6.966-7.340 (m, 4H), 7.638-7.667 (m, 2H); $^{13}$C NMR (CDCl$_3$, 100 MHz) δ 15.257, 55.762, 64.738, 82.219, 110.872, 117.093, 120.806, 126.206, 126.532, 129.261, 130.293, 136.770, 156.288; HRMS (m/z) calcd for $C_{13}H_{16}N_2O_2$ (M$^+$), 232.1206; found, 232.1209.

Characterization of 7: $^1$H NMR (CDCl$_3$, 400 MHz) δ 1.300 (t, 3H), 3.664 (m, 2H), 6.491 (s, 1H), 7.059 (s, 1H), 7.127 (s, 1H), 7.450-7.546 (m, 2H), 7.615-7.706 (m, 2H), 7.763 (s, 1H); $^{13}$C NMR (CDCl$_3$, 100 MHz) δ 14.926, 65.643, 85.159, 111.088, 116.643, 117.062, 126.209, 129.568, 130.139, 133.254, 136.386, 141.222; $^{13}$C NMR (Acetone-d$_6$, 100 MHz) δ 14.495, 65.035, 84.882, 111.161, 116.563, 117.125, 126.592, 129.744, 129.846, 133.435, 133.606, 137.071, 141.789; HRMS (m/z) calcd for $C_{13}H_{13}N_3O$ (M$^+$), 227.1053; found, 227.1055.

Characterization of 8: $^1$H NMR (CDCl$_3$, 400 MHz) δ 1.213 (t, 3H), 3.583 (m, 2H), 6.907 (s, 1H), 7.030 (s, 1H), 7.134 (s, 1H), 7.289 (d, 1H), 7.517-7.627 (m, 2H), 7.725 (s, 1H), 7.933 (d, 1H); $^{13}$C NMR (CDCl$_3$, 100 MHz) δ 14.683, 65.873, 83.735, 117.508, 125.062, 127.500, 130.140, 130.241, 132.873, 133.443, 136.940, 148.102; HRMS (m/z) calcd for $C_{12}H_{13}N_3O_3$ (M$^+$), 247.0951; found, 247.0950.

Synthesis of N-ethoxybenzylimidazole-doxorubicin Conjugate (9)

Compound 9 was synthesized using a synthetic route outlined in the following scheme S1.

Scheme S1. Synthetic scheme for N-ethoxybenzylimidazole-doxorubicin conjugate 9. Reagents: a) SOCl$_2$, ethanol; b) triethyl orthoformate, HCl, ethanol, 78% yield for two steps; c) SOCl$_2$, HOAc, neat; d) NaH, imidazole, THF, 33% yield for two steps; e) NaOH, THF/H$_2$O, 90% yield; f) doxorubicin, EDC, THF, 54% yield.

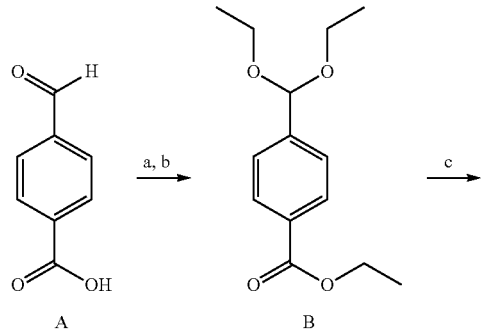

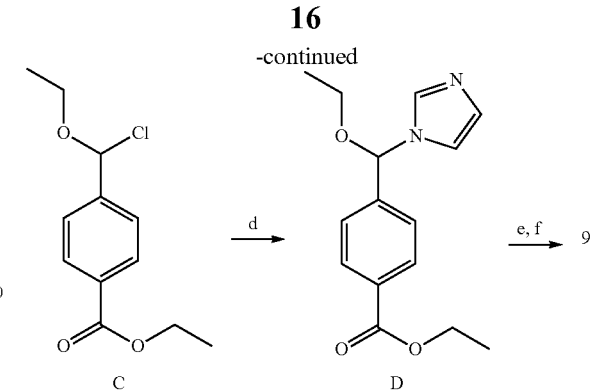

4-carboxylbenzaldehyde (A) (13.5 mmols) and thionyl chloride (27 mmols) was refluxed in 50 mL anhydrous dichloromethane (DCM) and 20 mL distilled ethanol for 12 hours. An additional 3 mL of thionyl chloride (41 mmols) was added and the solution was allowed to reflux for another 24 hours. The solution was cooled and the solvents were removed under reduced pressure. The product mixture was dissolved in DCM and washed with 10% sodium bicarbonate. The organic layer was dried over anhydrous Na$_2$SO$_4$. Crude NMR indicated a mixture of B and ethyl 4-formylbenzoate and was taken on without further purification.

The crude mixture of B and ethyl 4-formylbenzoate was combined with triethyl orthoformate (44.5 mmol) and conc. HCl (19.5 μL, 178 μmol) in 2.59 mL of absolute ethanol and allowed to reflux for 24 hours. After removal of ethanol and excess orthoformic acid under reduced pressure, the crude mixture was taken up in diethyl ether and the solution was washed with 2M NaOH. The organic layer was dried over anhydrous Na$_2$SO$_4$, and the diethyl ether was removed under reduced pressure. Compound B was distilled from the crude mixture under vacuum (141° C., 0.7 Torr) to give pure compound (78% isolated yield from A). Characterization of B: $^1$H NMR (CDCl$_3$, 400 MHz) δ 1.170 (t, 6H), 1.318 (t, 3H), 3.481 (m, 4H), 4.295 (q, 2H), 5.476 (s, 1H), 7.478 (d, 2H), 7.969 (d, 2H) $^{13}$C NMR (CDCl$_3$, 100 MHz) δ 14.465, 15.316, 61.157, 100.956, 126.834, 129.587, 130.526, 144.045, 166.411 ESI-MS: 224.96 (M$^+$-ethyl), 206.99 (M$^+$-ethoxy).

The synthesis of C was performed in using a modified procedure as previously reported (76). A solution of B (1.13 mmol), freshly distilled acetyl chloride (1.8 mmol) and thionyl chloride (0.227 mmol) was refluxed for one hour under N$_2$. The excess thionyl chloride and acetic acid were removed under reduced pressure and the crude mixture was characterized by $^1$H NMR. $^1$H-NMR (in CDCl$_3$) indicated a new peak at δ=6.203 ppm, presumably corresponding to the benzylic H in C. The crude yield of C by $^1$H-NMR was ~54%, with the remainder of the material identified as starting material B (~8%) as well as a large amount (~38%) of ethyl 4-formylbenzoate. The crude material was immediately taken on to the next step without further purification. Hydrolysis of C (presumably with moisture in the air) was observed over the course of several hours when left open to air. Compound C should, therefore, be prepared fresh and used immediately.

In a thy flask, NaH (0.612 mmol) and imidazole (0.612 mmol) was allowed to stir for one hour in 0.5 mL of anhydrous THF. A solution of a crude mixture of C (0.612 mmols) was added to the imidazole solution. The solution was stirred for 12 hours at 23° C. After removal of the solvent under reduced pressure, D was isolated by silica chromatography using as eluent a 95:5 mixture of DCM:methanol. The isolated yield of D was 33%. Characterization of E: $^1$H NMR (MeOH, 400 MHz) δ 1.270 (t, 3H), 1.368 (t, 3H), 3.526 (m, 1H), 3.674 (m, 1H), 4.358 (q, 2H), 6.527 (s, 1H), 7.089 (d, 2H), 7.509 (d, 2H), 7.946 (s, 1H), 8.034 (d, 2H). $^{13}$C NMR (MeOH, 100 MHz) δ 15.621, 15.158, 62.349, 65.760, 87.583, 118.570, 127.252, 129.949, 130.777, 132.216, 138.103, 144.535, 167.464 ESI-MS: 274.54 (M+H$^+$)

A solution of the D (0.151 mmol) and LiOH (0.151 mmol) in 0.8 mL of a 5:3 tetrahydrofuran (THF):water solution was allowed to stir for 12 hrs at 23° C. The THF and water were removed under reduced pressure and the crude solid was washed with chloroform. $^1$H-NMR of the crude in CD$_3$OD indicated only the desired carboxylate was present (presumably as the lithium salt). The yield was estimated as 90% by weight.

The crude mixture from ester hydrolysis of D (0.134 mmol) was dissolved in 1.5 mL dimethylformamide (DMF). Doxorubicin (16.7 μmol) and 1-(3-dimethylaminopropyl)-3-ethylcarbodiimide hydrochloride (EDC, 66.8 mmol) were added to the DMF solution and stirred for 12 hours at 23° C. Product 9 was isolated by silica chromatography using as eluent a 92:8 mixture of DCM:methanol. The isolated yield of 9 was 54%. Characterization of 9: $^1$H NMR (MeOH, 400 MHz) δ 1.242 (t, 3H), 1.283 (m, 6H), 1.833 (d, 1H), 2.136 (m, 2H), 2.356 (d, 1H), 2.915 (d, 1H), 3.017 (d, 1H), 3.491 (m, 1H), 3.635 (m, 1H), 3.741 (s, 1H), 3.955 (s, 3H), 4.326 (t, 2H), 4.753 (d, 2H), 5.069 (s, 1H), 5.435 (s, 1H), 5.492 (s, 1H), 6.471 (s, 1H), 6.990 (s, 1H), 7.081 (s, 1H), 7.433 (m, 3H), 7.740 (t, 1H0, 7.809 (d, 3H), 7.885 (s, 1H). HRMS (m/z) calcd for C$_{40}$H$_{42}$O$_{13}$N$_3$ (M+H$^+$) 772.2712; found, 772.2721.

Synthesis of N-(4-formylbenzoyl)doxorubicin (10)

Doxorubicin (6.9 μmol) was stirred in 660 μL of acetonitrile and 340 μL of water. 4-carboxybenzaldehyde (13.8 μmol), and EDC (17.6 μmol) were added to the solution and the solution was stirred for 18 hours at 23° C. Product 10 was isolated by silica chromatography using as eluent a 90:10 mixture of DCM:methanol. The isolated yield of 10 was 51%.

Characterization of 10: $^1$H NMR (CDCl$_3$, 300 MHz) δ 1.341 (s, 3H) 1.873 (d, 1H), 2.004 (m, 2H), 2.172 (d, 1H), 2.227 (d, 1H), 2.353 (d, 1H), 3.103 (d, 1H), 3.301 (d, 1H), 3.760 (s, 1H), 4.266 (m, 1H), 4.788 (s, 3H), 5.337 (d, 1H), 5.556 (d, 1H), 6.519 (d, 1H), 7.416 (d, 1H), 7.800 (t, 1H), 7.919 (m, 5H), 8.051 (d, 1H), 10.064 (s, 1H). ESI-MS: 698.01 (M+Na$^+$)

General Procedure for Hydrolysis of N-ethoxybenzylimidazole Derivatives (1-8)

1-8 (0.05 mmol) were placed in 0.5 mL of 0.5 M 2-[N-morpholino]ethanesulfonic acid (MES) buffer (pH=5.5) or 0.5 M N-[2-hydroxyethyl]piperazine-N'-[2-ethanesulfonic acid] (HEPES) buffer (pH=7.4) containing 20-40% DMSO-d$_6$ (v/v) and incubated at 37° C. in a constant temperature bath. The rates of hydrolyses were obtained by $^1$H-NMR measurements. The relative $^1$H NMR integrations of the benzylic protons of 1-8 and the aldehyde proton of the benzaldehyde product resulting from hydrolysis were compared over the time in order to estimate the rate of hydrolysis for the N-ethoxybenzylimidazoles.

Hydrolysis of N-ethoxybenzylimidazole Conjugated with Doxorubicin (9)

The N-ethoxybenzylimidazole conjugated with Doxorubicin (9) (0.37 μmol) was dissolved in 0.5 mL of 18.6 mM MES buffer (pH=5.5) or 18.6 mM HEPES buffer (pH=7.4) containing 30% DMSO (v/v) and incubated at 37° C. in a constant temperature bath. The hydrolysis of 9 at pH=5.5 and pH=7.4 was monitored by RP-HPLC by injection of small aliquots (20 μL) of the solutions at regular time intervals and analyzing the chromatograms at λ =470 nm. The products were eluted with an isocratic solvent mixture of 70% MeOH and 30% H$_2$O with a flow rate of 1 mL/min. The retention time of 9 and 10 were 6.25 minutes and 8.11 minutes, respectively. The rates of hydrolysis of the N-ethoxybenzylimidazole moiety in 9 were determined by comparison of the relative integrated HPLC peak areas of 9 and 10 at each time point.

Example 3

Cytotoxicity Studies of 10 on Human Ovarian Carcinoma 2008 Cells

Human ovarian carcinoma 2008 cells were plated in 6-well plates at a density of 200 cells in 3 mL of media (RPMI-1640+ 10% Fetal Bovine Serum) per well and incubated overnight to allow the cells to adhere to the bottom of the wells. After overnight incubation the media was removed from each well and fresh growth media containing different concentrations of 10 was added to the wells. The cells were incubated for 1 hour in the presence of 10. Following the removal of the solutions containing 10, the cells were incubated with fresh media for 10 days to allow surviving cells to form colonies. After removal of media, the plates were washed with 2 mL of room temperature PBS buffer (pH 7.4, 0.138 M NaCl, 0.003 mM KCl, 14.2 mM potassium phosphate), and then fixed and stained for 15 minutes with 1 mL of 0.1% crystal violet solution that contains 10% methanol. Clusters containing >50 cells were scored as colonies using an AlphaInontech Imager. The colony formation assay was performed in triplicate on 3 independent occasions.

Example 4

Comparison of Rates of Hydrolysis of N-ethoxybenzylimidazoles

To investigate whether electronic effects might influence the rate of hydrolysis of N-ethoxybenzylimidazoles, electron donating and electron withdrawing groups were incorporated at the ortho or para positions of the phenyl ring and the rates of hydrolysis were compared for 1-8. Incorporation of an electron donating methoxy group at the ortho position in 6, for instance, resulted in a half-life of 0.6 hours for the hydrolysis of 6 at 37° C. in 0.5 M MES in D$_2$O (pD=25.5); a slower rate of hydrolysis was observed for 6 (t1/2≈5 hours) at 37° C. in 0.5 M HEPES in D$_2$O (pD=7.4) compared to the rates of hydrolysis at pD=5.5 (Table 1).

Incorporation of electron withdrawing substituents at the ortho or para positions of the phenyl ring of 1, on the other hand, resulted in slower rates of hydrolysis in acidic and neutral solutions. Incorporation of a relatively weak electron withdrawing bromo substituent at the ortho position in 5, for example, resulted in a significant decrease in the rate of cleavage of the N-ethoxybenzylimidazole moiety, with measured half-lives of 280 and 2300 hours for the hydrolysis of 5 at 37° C. in buffered D$_2$O at pD=5.5 and pD=7.4, respectively. Furthermore, incorporation of strong electron withdrawing nitro substituents at the ortho or para position of the phenyl ring resulted in remarkably slow rates of hydrolysis of the N-ethoxybenzylimidazole moiety at 37° C., with measured half-lives of 6900 hours for both 3 and 8 in buffered D$_2$O at pD=5.5 and no hydrolysis detected after >8 weeks at pD=7.4.

Without limiting the present invention to any particular mode of action, to further probe the mechanism for cleavage of N-ethoxybenzylimidazoles in acidic solutions, the linear free energy relationship (Carroll, F. A., Perspectives on Structure and Mechanism in Organic Chemistry, Brooks/Cole Publishing Company; Pacific Grove, 1998) was plotted for the hydrolysis of 1-4 in $D_2O$ at pD=5.5. (FIG. 3) A ρ-value of −4.2 was calculated for the hydrolysis of the N-ethoxybenzylimidazoles, which is consistent with an increase in positive charge (e.g., on the benzylic carbon of 1-8) in the rate determining step of the reaction. This observed linear Hammett correlation, combined with the finding that the rate of hydrolysis of 1 is independent of the concentration of buffering agent [53], supports a specific acid catalyzed mechanism (Carroll, F. A., Perspectives on Structure and Mechanism in Organic Chemistry, Brooks/Cole Publishing Company; Pacific Grove, 1998) for the hydrolysis of 1-8 as shown in FIG. 1.

It appears that the n-ethoxybenzylimidazoles hydrolyze in aqueous solutions at physiological temperatures with hydrolysis occurring approximately 10 times faster in acidic solutions compared to solutions at normal, physiological pH. By incorporating electron donating or electron withdrawing substituents, the ability to tune the rates of hydrolysis of these N-linked imidazoles in mild acidic solutions with half-lives ranging from about 30 minutes to more than 9 months was demonstrated.

Example 5

Acid-Tunable Linkers Linked to Doxorubicin

Figure 4:
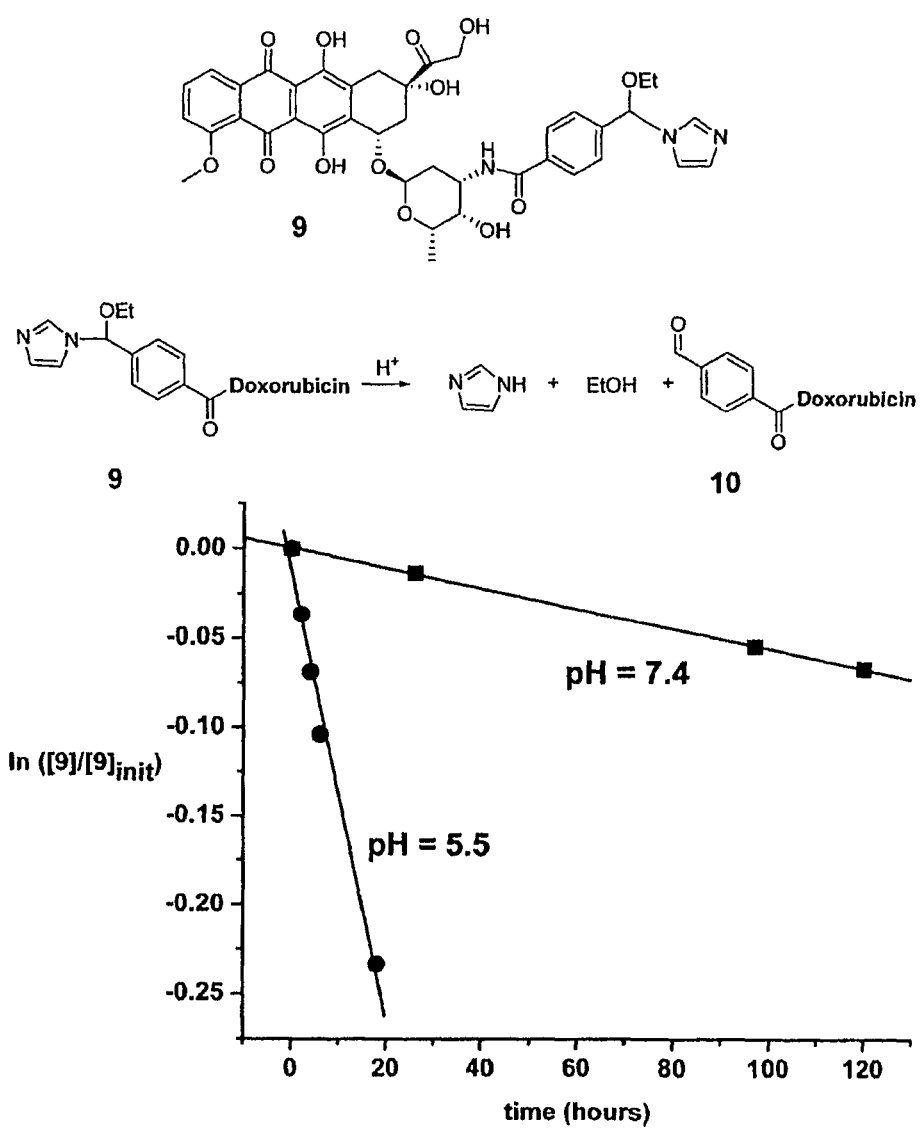
FIG. 4 is a graph of hydrolysis of an N-ethoxybenzylimidazole conjugated with doxorubicin 9 in MES buffer (pH=5.5) and HEPES buffer (pH=7.4). The pH-dependent rate of hydrolysis of 9 to aldehyde 10 was determined by RP-HPLC.
Figure 5:
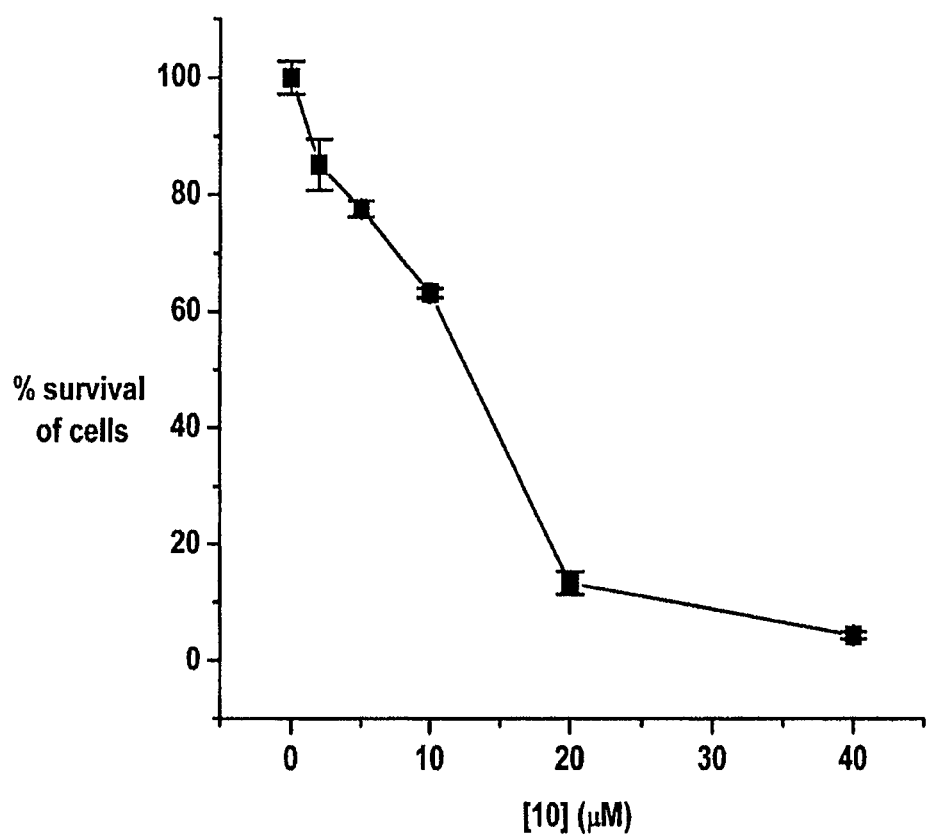
FIG. 5 is a graph of concentration-dependent cytotoxicity of N-(4-formylbenzoyl)doxorubicin 10 on human ovarian carcinoma 2008 cells. Cells were exposed to various concentrations of 10 for 1 hour and survival was determined after a further 7 day period of growth in drug-free medium.
Figure 6:
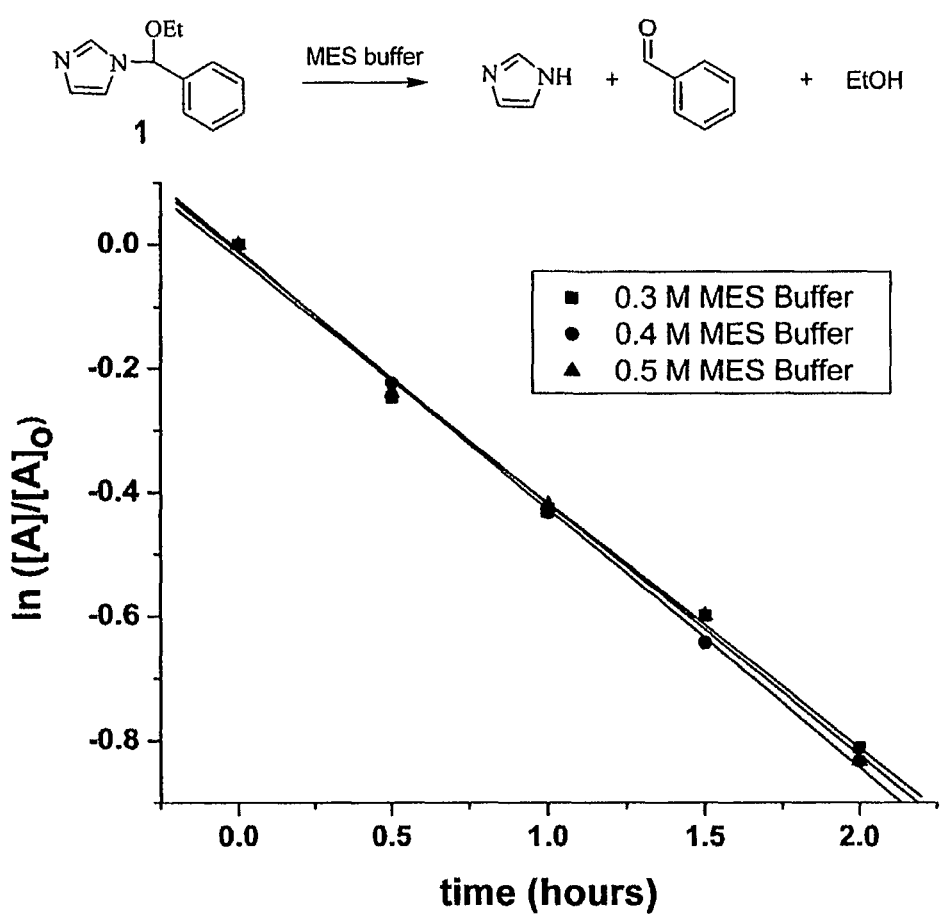
FIG. 6 is a graph of the dependence of the concentration of MES buffer on the rates of hydrolysis of N-ethoxybenzylimidazole 1. NaCl was added to solutions containing less than 0.5 M MES buffer to maintain a constant ionic strength for all measurements. Solutions of 1 (50 mM) in buffered $D_2O$ solutions containing 20% $d_6$-DMSO (v/v) were incubated in a 37° C. constant temperature bath. Rates of hydrolyses were obtained by $^1H$-NMR (400 MHz) measurements.

An n-ethoxybenzylimidazole carrying an antitumour agent, doxorubicin (77), was tested for its ability to hydrolyze with accelerated rates under mild acidic solutions compared to at normal, physiological pH. 9 was synthesized by formation of an amide bond between a reactive amine group on doxorubicin and a carboxylate group on the para position of the phenyl ring of the n-ethoxybenzylimidazole (FIG. 4). Details of the synthesis and characterization of 9 are presented in the present set of Examples. A half-life was measured by RP-HPLC of 55 hours for the hydrolysis of 9 at 37° C. in MES buffered $H_2O$ (pH=5.5) The observed rate of hydrolysis of 9 at pH=5.5 is consistent with the expected value for an n-ethoxybenzylimidazole group containing an amide functionality attached to the para position of the phenyl ring in 1 as predicted from the linear free energy relationship shown in FIG. 4 (R=CONHR', σ=0.36, log $(k_R/k_H)$=−1.32) As expected, a slower rate of hydrolysis of 9 was observed ($t_{1/2}$=1150 hours) at 37° C. in HEPES buffered $H_2O$ (pH=7.4) compared to the rates of hydrolysis at pH=5.5 (FIG. 4). Cytotoxicity studies indicated that 10 (i.e., the analogue of doxorubicin resulting from hydrolysis of 9 in mild acidic solutions) retains anticancer activity against human ovarian carcinoma 2008 cells with an $IC_{50}$ of about 12 μM (FIG. 5). For comparison, compound 9 had a 2-fold higher $IC_{50}$, and doxorubicin had a >10-fold lower $IC_{50}$ than 10 against this cell line. Although less potent than a doxorubicin, compound 10 also has similar cytotoxic activity compared to other clinically used anticancer agents being developed for controlled release from drug delivery systems via pH-sensitive linkers (75).

N-ethoxybenzylimidazoles thus hydrolyze in aqueous solutions at physiological temperatures with hydrolysis occurring approximately 10 times faster in mildly acidic solutions compared to solutions at normal, physiological pH. By incorporating electron donating or electron withdrawing substituents, the ability to tune the rates of hydrolysis of these N-linked imidazoles in mild acidic solutions was demonstrated with half-lives ranging from about 30 minutes to greater than 9 months. A n-ethoxybenzylimidazole carrying doxorubicin also exhibited accelerated rates of hydrolysis in acidic solution compared to at neutral pH, with the product of hydrolysis showing potentially useful cytotoxic activity against human cancer cells. Previous studies have shown that drugs conjugated to delivery vessels via pH-sensitive linkers with hydrolytic properties similar to those of 9 can exhibit useful antitumor activity in vivo. (48). These drugs conjugated to delivery vessels using pH-sensitive linkers also showed reduced toxicity to normal, healthy tissues compared to administration of equivalent concentrations of free drug. The ability to tune the rates of hydrolysis of the n-ethoxybenzylimidazoles may make it possible to optimize the rate of release of drugs attached to delivery vessels via these acid-sensitive functionalities for maximal efficacy for cancer therapy.

The N-linked imidazoles provided herein possess many desired features for use as acid sensitive linkers in drug and imaging agent delivery, including, for example, for cancer drug delivery. In addition to their tunable rates of hydrolysis, their nontoxic byproducts from hydrolysis (i.e., ethanol), and their versatility for the range of alcohol- and amine-containing therapeutics that can be linked to drug carriers, the known ability to tune the $pK_a$s of protonated imidazoles may make it possible to optimize the operational pH range of these linkers for specific drug delivery applications. The mild conditions required to synthesize these linkers carrying anticancer agents also provides a simple route to incorporate this functionality into tumor-targeting vessels. It may be possible, for instance, to use these linkers to covalently attach therapeutics to imidazole containing derivatives of known delivery systems that can target tumors and exploit the endocytotic pathway for internalization in cells.

TABLE 1

Half-lives ($t_{1/2}$) and rate constants (k) for the hydrolysis of N-ethoxybenzylimidazoles in $D_2O$ at pD = 5.5 and pD = 7.4. Rates of hydrolyses were measured by $^1$H-NMR.

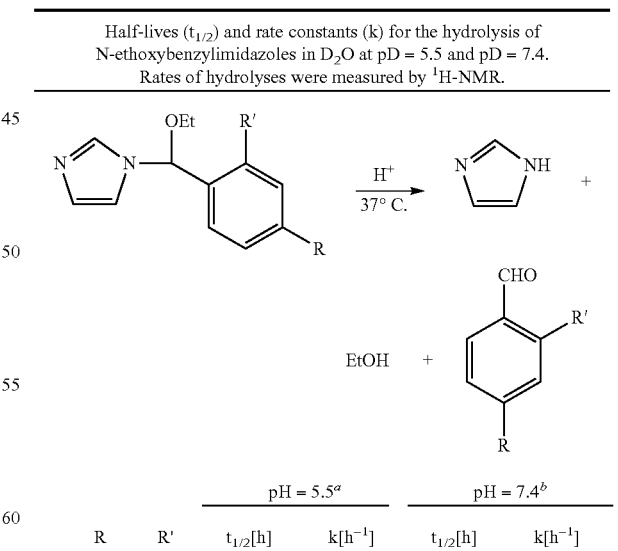

| | | | pH = 5.5[a] | | pH = 7.4[b] | |
|---|---|---|---|---|---|---|
| | R | R' | $t_{1/2}$[h] | k[h$^{-1}$] | $t_{1/2}$[h] | k[h$^{-1}$] |
| 1 | H | H | 1.7 | 0.41 | 25 | 0.028 |
| 2 | Br | H | 16.2 | 0.04 | 270 | 0.003 |
| 3 | $NO_2$ | H | 6900 | <0.001 | N/A[c] | — |
| 4 | Bu | H | 1.0 | 0.69 | 8.8 | 0.079 |
| 5 | H | Br | 280 | 0.003 | 2310 | <0.001 |

TABLE 1-continued

| 6 | H | OMe | 0.6 | 1.13 | 5.1 | 0.136 |
| 7 | H | CN | 3500 | <0.001 | N/A[c] | — |
| 8 | H | NO$_2$ | 6900 | <0.001 | N/A[c] | — |

[a]0.5M MES buffer solution
[b]0.5M HEPES buffer
[c]No hydrolysis detected after >8 weeks

Example 6

Additional Examples of N-alkoxy-alkylimidazoles

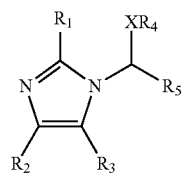

Further examples of N-alkoxy-alkylimidazoles include those in the following Table 2. In these examples, $R_1$, $R_2$, and $R_3$ are H, $XR_4$ is OEt, $R_a$ is a hydroxyl-containing therapeutic or imaging agent, $R_9$ is an amine-containing therapeutic or imaging agent, and $R_6$ and $R_7$ are as shown in the table:

TABLE 2

| entry | $R_6$ | $R_7$ |
|---|---|---|
| 1 | H | H |
| 2 | Br | H |
| 3 | NO$_2$ | H |
| 4 | Butyl | H |
| 5 | COR$_8$ | H |
| 6 | COR$_9$ | H |
| 7 | H | Br |
| 8 | H | OMethyl |
| 9 | H | CN |
| 10 | H | COR$_8$ |
| 11 | H | COR$_9$ |

Example 7

Cytotoxicity Studies of Therapeutics

Examples of therapeutics, including cancer therapeutics that can be released from N-alkoxy-alkylimidazoles are presented as therapeutic derivatives 2, 4, and 6 below. Also presented are related therapeutics 1, 3, and 5.

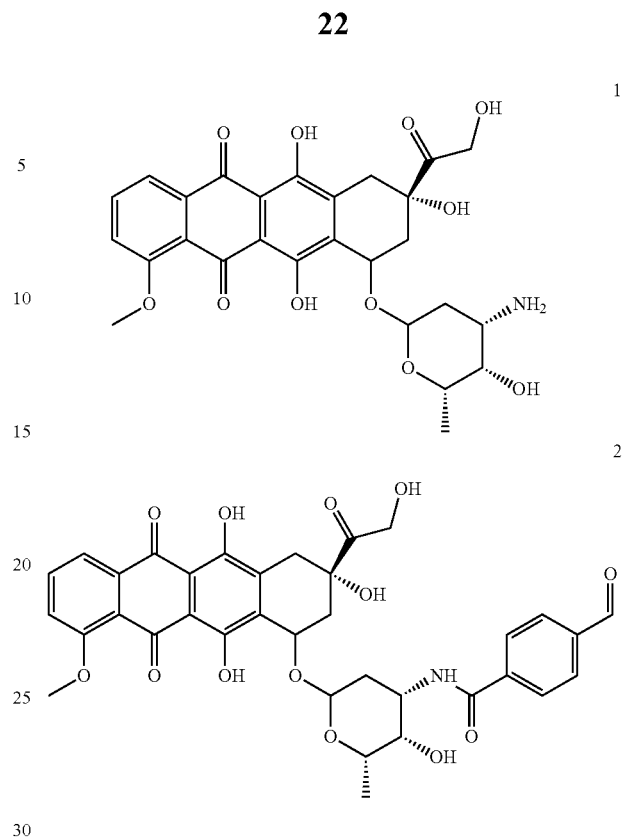

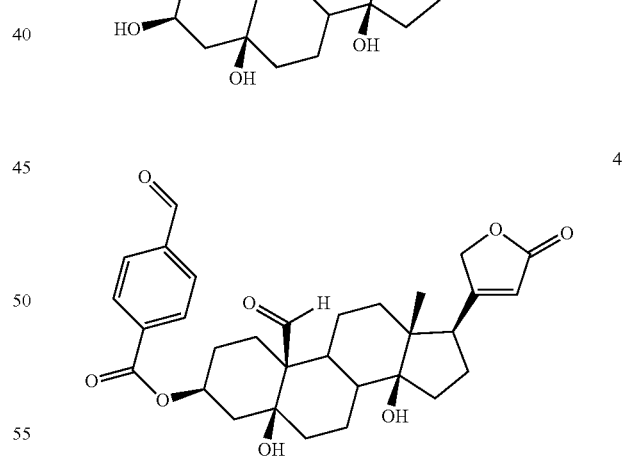

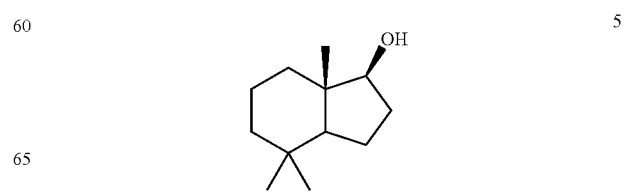

-continued

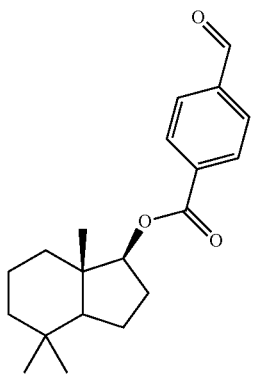

Cytotoxicity studies of therapeutics 1, 3, and 5, and therapeutic derivatives 2, 4, and 6 on human ovarian carcinoma 2008 cells are shown in Table 3.

TABLE 3

| Molecule | IC$_{50}$ (μM) |
| --- | --- |
| 1 | 0.01 |
| 2 | 9.0 |
| 3 | 0.1 |
| 4 | 0.25 |
| 5 | 52 |
| 6 | 55 |

Synthesis of therapeutic derivatives 2, 4, and 6 is as follows:
Synthesis of 2
Doxorubicin (1, 6.9 μmol) was dissolved in 0.66 μL of acetylnitrile and 0.34 μL of water. 4-carboxylbenxaldehyde (13.8 μmol) and (1-ethyl-3-(3-dimethylaminopropyl) carbodiimide hydrochloride (EDC, 13.8 μmol) were added to the solution and stirred for 12 hours at 23° C. Product was purified by column chromatography, 10% Methanol (MeOH) in dichloromethane (DCM), isolated yield 51%.
Synthesis of 4
Strophanthidin (3, 35 μmol) was dissolved in 0.5 mL of dichloromethane (DCM). 4-carboxybenzaldehye (95 μmol), N,N'-dicyclohexylcarbodiimide (DCC, 89 μmol) and Dimethylaminopyridine (DMAP, 1 crystal) was added and stirred overnight at 23° C. The product was purified by column chromatography, 7% MeOH in DCM, isolated yield 10%.
Synthesis of 6
Norrisolide core (5) was synthesized as described in Brady, T.; Kim, S.; Wen, K.; Theodorakis, E. A. *Angew. Chem. Int. Ed.* 2004, 43, 739-742. Norrisolide Core (5, 11 μmol) was dissolved in 0.5 mL of dichloromethane (DCM). 4-carboxybenzaldehye (19 μmol), N,N'-dicyclohexylcarbodiimide (DCC, 19 μmol) and Dimethylaminopyridine (DMAP, 1 crystal) was added and stirred overnight at 23° C. The product was purified by column chromatography in DCM, isolated yield 78.1%.
Cytotoxicity studies were performed as described in S. D. Kong, A. Luong, G. Manorek, S. B. Howell, and J. Yang* *Bioconjugate Chem.*, 2007, 18, 293-296.

Example 8

N-dialkoxyalkylimidazole Derivatives

N-dialkoxyimidazole derivatives were synthesized as shown in the following scheme, and found to be acid sensitive.

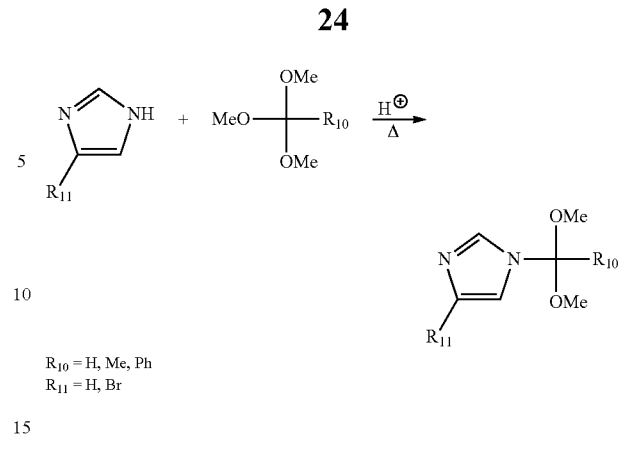

R$_{10}$ = H, Me, Ph
R$_{11}$ = H, Br

General Procedure for the Synthesis of N-dialkoxyalkylimidazoles(WW-ZZ)

A mixture of 4-substituted imidazole (44 mmol), trimethoxymethylalkane (176 mmol), and p-toluenesulfonic acid (1.3 mmol) was heated 95° C. for 1-2 days, accompanied by concurrent distillation of methanol. After cooling, sodium carbonate (11 mmol) was added and the crude mixture was distilled under vacuum (95° C.-160° C.) to give N-dialkoxyalkylimidazole derivatives (1-4) (20-46% yield).
Characterization of WW (R$_{10}$=H, R$_{11}$=H): $^1$H NMR (CDCl3, 400 MHz) 2.945 (s, 6H), 5.560 (s, H), 6.677 (s, 2H), 7.321 (s, 1H) GC-MS RT=5.04; MS (m/z) 111.4 (M+–OMe)
Characterization of XX (R$_{10}$=Me, R$_{11}$=H): $^1$H NMR (CDCl3, 400 MHz) 1.707 (s, 3H), 3.198 (s, 6H), 7.016 (s, 2H), 7.704 (s, 1H) GC-MS RT=5.40; MS (m/z) 125.3 (M$^+$-OMe)
Characterization of YY (R$_{10}$=Ph, R$_{11}$=H): $^1$H NMR (CDCl3, 400 MHz) 3.164 (s, 6H), 6.990-7.851 (m, 8H) GC-MS RT=9.28; MS (m/z) 187.3 (M$^+$-OMe)
Characterization of ZZ (R$_{10}$=Me, R$_{11}$=Br): $^1$H NMR (CDCl3, 400 MHz) 1.695 (s, 3H), 3.213 (s, 6H), 6.991 (s, 1H), 7.573 (s, 1H) GC-MS RT=8.00; MS (m/z) 203.4 (M$^+$-OMe)

General Procedure for Hydrolysis of N-dialkoxyalkylimidazoles(WW-ZZ)

1-4 (0.05 mmol) were placed in 0.5 mL of 0.5 M 2-[N-morpholino]ethanesulfonic acid (MES) buffer (pH=5.5) or 0.5 M N-[2-hydroxyethyl]piperazine-N'-[2-ethanesulfonic acid] (HEPES) buffer (pH=7.4) containing 20-40% DMSO-d6 (v/v) and incubated at 37° C. in a constant temperature bath. The rates of hydrolyses were obtained by 1H-NMR measurements. Result: hydrolyzed completely in <30 min. in all cases but are generally faster in acidic solutions compared to neutral or basic solutions

REFERENCES

1. Gonmori, K., and Kuroiwa, Y. (1974). Measurement of Intracellular Ph on Tumor-Cells. Folia Pharmacologica Japonica 70, P14-P15.
2. Ferraretto, A., Sonnino, S., Soria, M. R., and Masserini, M. (1996). Characterization of biotinylated liposomes sensitive to temperature and pH: New tools for anti-cancer drug delivery. Chemistry and Physics of Lipids 82, 133-139.
3. Seachrist, L. (1993). Researchers Engineering New Cancer Drug-Delivery Systems. Journal of the National Cancer Institute 85, 1797-1798.

4. Gabizon, A. (1993). Tailoring Liposomes for Cancer Drug-Delivery—from the Bench to the Clinic. Armies De Biologie Clinique 51, 811-813.

5. Na, K., Lee, T. B., Park, K. H., Shin, E. K., Lee, Y. B., and Cho, H. K. Self-assembled nanoparticles of hydrophobically-modified polysaccharide bearing vitamin H as a targeted anti-cancer drug delivery system. European Journal of Pharmaceutical Sciences, 165-173.

6. Mi, F. L., Lin, Y. M., Wu, Y. B., Shyu, S. S., and Tsai, Y. H. Chitin/PLGA blend microspheres as a biodegradable drug-delivery system: phase-separation, degradation and release behavior. Biomaterials, 3257-3267.

7. Liu, X. Y., Gao, C. Y., Shen, J. C., and Mohwald, H. (2005). Multilayer microcapsules as anti-cancer drug delivery vehicle: Deposition, sustained release, and in vitro bioactivity. Macromolecular Bioscience 5, 1209-1219.

8. Jain, K. K. (2005). Targeted drug delivery for cancer. Technology in Cancer Research & Treatment 4, 311-313.

9. Cay, O., Kruskal, J. B., Nasser, I., Thomas, P., and Clouse, M. E. (1997). Liver metastases from colorectal cancer: Drug delivery with liposome-encapsulated doxorubicin. Radiology 205, 95-101.

10. Tao, S. L., and Desai, T. A. (2003). Microfabricated drug delivery systems: from particles to pores. Advanced Drug Delivery Reviews 55, 315-328.

11. Tao, S. L., Lubeley, M. W., and Desai, T. A. (2003). Synthesis of cytoadhesive poly(methylmethacrylate) for applications in targeted drug delivery. Journal of Biomedical Materials Research Part A 67A, 369-375.

12. Tao, S. L., Lubeley, M. W., and Desai, T. A. (2003). Bioadhesive poly(methyl methacrylate) microdevices for controlled drug delivery. Journal of Controlled Release 88, 215-228.

13. Leoni, L., and Desai, T. A. (2001). Nanoporous biocapsules for the encapsulation of insulinoma cells: Biotransport and biocompatibility considerations. Ieee Transactions on Biomedical Engineering 48, 1335-1341.

14. McAllister, D. V., Allen, M. G., and Prausnitz, M. R. (2000). Microfabricated microneedles for gene and drug delivery. Annual Review of Biomedical Engineering 2, 289-313.

15. Chen, J. K., and Wise, K. D. (1997). A silicon probe with integrated microheaters for thermal marking and monitoring of neural tissue. IEEE Transactions on Biomedical Engineering 44, 770-774.

16. Chen, J. K., Wise, K. D., Hetke, J. F., and Bledsoe, S. C. (1997). A multichannel neural probe for selective chemical delivery at the cellular level. IEEE Transactions on Biomedical Engineering 44, 760-769.

17. Davis, S. S., and Illum, L. (1998). Drug delivery systems for challenging molecules. International Journal of Pharmaceutics 176, 1-8.

18. Yoo, H. S., Lee, K. H., Oh, J. E., and Park, T. G. (2000). In vitro and in vivo anti-tumor activities of nanoparticles based on doxorubicin-PLGA conjugates. Journal of Controlled Release 68, 419-431.

19. Reddy, L. H. (2005). Drug delivery to tumours: recent strategies. Journal of Pharmacy and Pharmacology 57, 1231-1242.

20. Rice, J. R., and Howell, S. B. (2004). AP-5346—Polymer-Delivered Platinum Complex. Drugs of the Future 29, 561-565.

21. Brown, D. M. (2004). Drug Delivery Systems in Cancer Therapy (Totowa: Humana Press).

22. Desai, N., Campbell, K. J., Ellerhorst, J., Ibrahim, N., and Soon-Shiong, P. (2002). Preclinical and clinical pharmacokinetics and safety of ABI-007, a novel, cremophor-free, protein-engineered nanotransporter of paclitaxel. Breast Cancer Research and Treatment 76, S131-S131.

23. Damascelli, B., Patelli, G. L., Lanocita, R., Di Tolla, G., Frigerio, L. F., Marchiano, A., Garbagnati, F., Spreafico, C., Ticha, V., Gladin, C. R., Palazzi, M., Crippa, F., Oldini, C., Cabo, S., Bonaccorsi, A., Mattavelli, F., Costa, L., Mariani, L., and Cantu, G. (2003). A novel Intraarterial chemotherapy using paclitaxel in albumin nanoparticles to treat advanced squamous cell carcinoma of the tongue: Preliminary findings. American Journal of Roentgenology 181, 253-260.

24. LaVan, D. A., Lynn, D. M., and Langer, R. (2002). Moving smaller in drug discovery and delivery. Nature Reviews Drug Discovery 1, 77-84.

25. Ibrahim, N. K., Desai, N., Legha, S., Soon-Shiong, P., Theriault, R. L., Rivera, E., Esmaeli, B., Ring, S. E., Bedikian, A., Hortobagyi, G. N., and Ellerhorst, J. A. (2002). Phase I and pharmacokinetic study of ABI-007, a cremophor-free, protein-stabilized, nanoparticle formulation of paclitaxel. Clinical Cancer Research 8, 1038-1044.

26. Ibrahim, N. K., Samuels, B., Page, R., Doval, D., Patel, K. M., Rao, S. C., Nair, M. K., Bhar, P., Desai, N., and Hortobagyi, G. N. (2005). Multicenter phase II trial of ABI-007, an albumin-bound paclitaxel, in women with metastatic breast cancer. Journal of Clinical Oncology 23, 6019-6026.

27. Dvorak, H. F., Nagy, J. A., Dvorak, J. T., and Dvorak, A. M. (1988). Identification and Characterization of the Blood-Vessels of Solid Tumors That Are Leaky to Circulating Macromolecules. American Journal of Pathology 133, 95-109.

28. Baluk, P., Hashizume, H., and McDonald, D. M. (2005). Cellular abnormalities of blood vessels as targets in cancer. Current Opinion in Genetics & Development 15, 102-111.

29. Hashizume, H., Baluk, P., Morikawa, S., McLean, J. W., Thurston, G., Roberge, S., Jain, R. K., and McDonald, D. M. (2000). Openings between defective endothelial cells explain tumor vessel leakiness. American Journal of Pathology 156, 1363-1380.

30. Heffernan, M. J., and Murthy, N. (2005). Polyketal nanoparticles: A new pH-sensitive biodegradable drug delivery vehicle. Bioconjugate Chemistry 16, 1340-1342.

31. Gillies, E. R., and Frechet, J. M. J. (2005). pH-responsive copolymer assemblies for controlled release of doxorubicin. Bioconjugate Chemistry 16, 361-368.

32. Gelperina, S., Kisich, K., Iseman, M. D., and Heifets, L. (2005). The potential advantages of nanoparticle drug delivery systems in chemotherapy of tuberculosis. American Journal of Respiratory and Critical Care Medicine 172, 1487-1490.

33. Li, S. M. (1999). Hydrolytic degradation characteristics of aliphatic polyesters derived from lactic and glycolic acids. Journal of Biomedical Materials Research 48, 342-353.

34. Kreuter, J. (1991). Nanoparticle-Based Drug Delivery Systems. Journal of Controlled Release 16, 169-176.

35. Youichiro Noguchi, J. W., Ruth Duncan, Jiri Strohalm, Karel Ulbrich, Takaaki Akaike, Hiroshi Maeda (1998). Early Phase Tumor Accumulation of Macromolecules: A Great Difference in Clearance Rate between Tumor and Normal Tissues. Japanese Journal of Cancer Research 89, 307-314.

36. Sparreboom, A., Scripture, C. D., Trieu, V., Williams, P. J., De, T. P., Yang, A., Beals, B., Figg, W. D., Hawkins, M., and Desai, N. (2005). Comparative preclinical and clinical pharmacokinetics of a cremophor-free, nanoparticle albumin-bound paclitaxel (ABI-007) and paclitaxel formulated in cremophor (Taxol). Clinical Cancer Research 11, 4136-4143.

37. Nolan, C. M., Serpe, M. J., and Lyon, L. A. (2004). Thermally modulated insulin release from microgel thin films. Biomacromolecules 5, 1940-1946.

38. Ruebner, A., Yang, Z. W., Leung, D., and Breslow, R. (1999). A cyclodextrin dimer with a photocleavable linker as a possible carrier for the photosensitizer in photodynamic tumor therapy. Proceedings of the National Academy of Sciences of the United States of America 96, 14692-14693.

39. Husseini, G. A., Christensen, D. A., Rapoport, N. Y., and Pitt, W. G. (2002). Ultrasonic release of doxorubicin from Pluronic P105 micelles stabilized with an interpenetrating network of N,N-diethylacrylamide. Journal of Controlled Release 83, 303-305.

40. Marin, A., Sun, H., Husseini, G. A., Pitt, W. G., Christensen, D. A., and Rapoport, N. Y. (2002). Drug delivery in pluronic micelles: effect of high-frequency ultrasound on drug release from micelles and intracellular uptake. Journal of Controlled Release 84, 39-47.

41. Ojugo, A. S. E., McSheehy, P. M. J., Stubbs, M., Alder, G., Bashford, C. L., Maxwell, R. J., Leach, M. O., Judson, I. R., and Griffiths, J. R. (1998). Influence of pH on the uptake of 5-fluorouracil into isolated tumour cells. British Journal of Cancer 77, 873-879.

42. Ojugo, A. S. E., McSheehy, P. M. J., McIntyre, D. J. O., McCoy, C., Stubbs, M., Leach, M. O., Judson, I. R., and Griffiths, J. R. (1999). Measurement of the extracellular pH of solid tumours in mice by magnetic resonance spectroscopy: a comparison of exogenous F-19 and P-31 probes. NMR in Biomedicine 12, 495-504.

43. Gillies, E. R., Goodwin, A. P., and Frechet, J. M. J. (2004). Acetals as pH-sensitive linkages for drug delivery. Bioconjugate Chemistry 15, 1254-1263.

44. Minko, T., Paranjpe, P. V., Qiu, B., Lalloo, A., Won, R., Stein, S., and Sinko, P. J. (2002). Enhancing the anticancer efficacy of camptothecin using biotinylated poly(ethyleneglycol) conjugates in sensitive and multidrug-resistant human ovarian carcinoma cells. Cancer Chemotherapy and Pharmacology 50, 143-150.

45. Heller, J., Barr, J., Ng, S. Y., Abdellauoi, K. S., and Gurny, R. (2002). Poly(ortho esters): synthesis, characterization, properties and uses. Advanced Drug Delivery Reviews 54, 1015-1039.

46. Etrych, T., Jelinkova, M., Rihova, B., and Ulbrich, K. (2001). New HPMA copolymers containing doxorubicin bound via pH-sensitive linkage: synthesis and preliminary in vitro and in vivo biological properties. Journal of Controlled Release 73, 89-102.

47. Kruger, M., Beyer, U., Schumacher, P., Unger, C., Zahn, H., and Kratz, F. (1997). Synthesis and stability of four maleimide derivatives of the anticancer drug doxorubicin for the preparation of chemoimmunoconjugates. Chemical & Pharmaceutical Bulletin 45, 399-401.

48. Patel, V. F., Hardin, J. N., Mastro, J. M., Law, K. L., Zimmermann, J. L., Ehlhardt, W. J., Woodland, J. M., and Starling, J. J. (1996). Novel acid labile COL1 trityl-linked difluoronucleoside immunoconjugates: Synthesis, characterization, and biological activity. Bioconjugate Chemistry 7, 497-510.

49. Greenfield, R. S., Kaneko, T., Daues, A., Edson, M. A., Fitzgerald, K. A., Olech, L. J., Grattan, J. A., Spitalny, G. L., and Braslawsky, G. R. (1990). Evaluation In vitro of Adriamycin Immunoconjugates Synthesized Using an Acid-Sensitive Hydrazone Linker. Cancer Research 50, 6600-6607.

50. Shen, W. C., and Ryser, H. J. P. (1981). Cis-Aconityl Spacer between Daunomycin and Macromolecular Carriers—a Model of Ph-Sensitive Linkage Releasing Drug from a Lysosomotropic Conjugate. Biochemical and Biophysical Research Communications 102, 1048-1054.

51. Schmir, G. L., and Bruice, T. C. (1958). Imidazole Catalysis. 3. The Solvolysis of 4-(2'-Acetoxyphenyl)-Imidazole. Journal of the American Chemical Society 80, 1173-1177.

52. Manoharan, T. S., and Brown, R. S. (1988). 1-(1-Ethoxyethyl) an Effective Protecting Group for Imidazole Nitrogen. Journal of Organic Chemistry 53, 1107-1110.

53. Connors, K. A. (1990). Chemical Kinetics: The study of Reaction Rates in Solution (New York: Wiley-VCH).

54. Farquhar, D., Cherif, A., Bakina, E., and Nelson, J. A. (1998). Intensely potent doxorubicin analogues: Structure-activity relationship. Journal of Medicinal Chemistry 41, 965-972.

55. Nagy, A., Armatis, P., and Schally, A. V. (1996). High yield conversion of doxorubicin to 2-pyrrolinodoxorubicin, an analog 500-1000 times more potent: Structure-activity relationship of daunosamine-modified derivatives of doxorubicin. Proceedings of the National Academy of Sciences of the United States of America 93, 2464-2469.

56. Northfelt, D. W., Dezube, B. J., Thommes, J. A., Miller, B. J., Fischl, M. A., Friedman-Kien, A., Kaplan, L. D., Du Mond, C., Mamelok, R. D., and Henry, D. H. (1998). Pegylated-liposomal doxorubicin versus doxorubicin, bleomycin, and vincristine in the treatment of AIDS-related Kaposi's sarcoma: Results of a randomized phase III clinical trial. Journal of Clinical Oncology 16, 2445-2451.

57. Stewart, S., Jablonowski, H., Goebel, F. D., Arasteh, K., Spittle, M., Rios, A., Aboulafia, D., Galleshaw, J., and Dezube, B. J. (1998). Randomized comparative trial of pegylated liposomal doxorubicin versus bleomycin and vincristine in the treatment of AIDS-related Kaposi's sarcoma. Journal of Clinical Oncology 16, 683-691.

58. Sah, H., Toddywala, R., and Chien, Y. W. (1995). Continuous Release of Proteins from Biodegradable Microcapsules and in-Vivo Evaluation of Their Potential as a Vaccine Adjuvant. Journal of Controlled Release 35, 137-144.

59. Steinman, R. M., Mellman, I. S., Muller, W. A., and Cohn, Z. A. (1983). Endocytosis and the Recycling of Plasma-Membrane. Journal of Cell Biology 96, 1-27.

60. Gilding, D. K. (1981). Biodegradable Polymers, Williams, D. F. Edition (Boca Raton: CRC).

61. Tansini, C. M., Durigon, K., Testa, C. G., Bello-Klein, A., Wajner, M., Wannmacher, C. M. D., Wyse, A. T. S., and Dutra-Filho, C. S. (2004). Effects of histidine and imidazolelactic acid on various parameters of the oxidative stress in cerebral cortex of young rats. International Journal of Developmental Neuroscience 22, 67-72.

62. Jorgense. Ec, Windridg. Gc, and Lel, T. C. (1970). Angiotensin-Ii Analogs. 3. Synthesis and Biological Evaluation of Some Des-Aspartyl-Angiotensins. Journal of Medicinal Chemistry 13, 352

63. Felix, A. M., Heimer, E. P., Lambros, T. J., Tzougraki, C., and Meienhofer, J. (1978). Rapid Removal of Protecting Groups from Peptides by Catalytic Transfer Hydrogenation with 1,4-Cyclohexadiene. Journal of Organic Chemistry 43, 4194-4196.

64. du Vigneaud, V. (1936). A Method for Protecting the Imidazole Ring of Histidine During Certain Reactions and its Application to the Preparation of L-Amino-N-Methylhistidine. Journal of Biological Chemistry 117, 27-36.

65. Johnson, T., and Quibell, M. (1994). The N-(2-Hydroxybenzyl) Protecting Group for Amide Bond Protection in Solid-Phase Peptide-Synthesis. Tetrahedron Letters 35, 463-466.

66. Ouchi, T., and Fujino, A. (1989). Synthesis of Poly (Alpha-Malic Acid) and Its Hydrolysis Behavior In vitro. Makromolekulare Chemie-Macromolecular Chemistry and Physics 190, 1523-1530.

67. Kimura, Y., Shirotani, K., Yamane, H., and Kitao, T. (1988). Ring-Opening Polymerization of 3(S)-(Benzyloxycarbonyl)Methyl-1,4-Dioxane-2,5-Dione—a New Route to a Poly(Alpha-Hydroxy Acid) with Pendant Carboxyl Groups. Macromolecules 21, 3338-3340.

68. Shaabani, A., Mirzaei, P., Naderi, S., and Lee, D. G. (2004). Green oxidations. The use of potassium permanganate supported on manganese dioxide. Tetrahedron 60, 11415-11420.

69. Kreh, R. P., Spotnitz, R. M., and Lundquist, J. T. (1987). Selective Oxidations with Ceric Methanesulfonate and Ceric Trifluoromethanesulfonate. Tetrahedron Letters 28, 1067-1068.

70. Almlof, J. E., Feyereisen, M. W., Jozefiak, T. H., and Miller, L. L. (1990). Electronic-Structure and near-Infrared Spectra of Diquinone Anion Radicals. Journal of the American Chemical Society 112, 1206-1214.

71. Thompson, A. L. S., Kabalka, G. W., Akula, M. R., and Huffman, J. W. (2005). The conversion of phenols to the corresponding aryl halides under mild conditions. Synthesis-Stuttgart, 547-550.

72. Gavin, J. P., and Waigh, R. D. (1990). The Cyclization of Benzylaminonitriles. 7. Regiospecific Formation of Methoxy-Substituted Isoquinolin-4-Ones Using Methylthio Activating Groups. Journal of the Chemical Society-Perkin Transactions 1, 503-508.

73. Curtis, N. J., and Brown, R. S. (1980). An Easily Introduced and Removed Protecting Group for Imidazole Nitrogen—a Convenient Route to 2-Substituted Imidazoles. Journal of Organic Chemistry 45, 4038-4040.

74. Hwang, F. S., and Hogenesch, T. E. (1993). Fluorocarbon-Modified Water-Soluble Cellulose Derivatives. Macromolecules 26, 3156-3160.

75. Lin, X., Zhang, Q., Rice, J. R., Stewart, D. R., Nowotnik, D. P., and Howell, S. B. (2004) Improved targeting of platinum chemotherapeutics: The antitumour activity of HPMA copolymer platinum agent AP5280 in murine tumour models. Eur. J. Cancer 40, 291-297.

76. Capon, B., Nimmo, K. (1975) General acid-catalyzed hydrolysis of benzaldehyde aryl methyl acetals J. Chem. Soc., Perkin Trans. 2, 10, 1113-1118.

77. Perry, M. C., (2001) The Chemotherapy Source Book, 3$^{rd}$ ed., Lipincott, Williams & Wilkins, Philadelphia; Arcamone, F. (1981) Doxorubicin Anticancer Antibiotics, Academic Press, New York.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Singular forms "a", "an", and "the" include plural reference unless the context clearly dictates otherwise. Thus, for example, reference to "a subset" includes a plurality of such subsets, reference to "a nucleic acid" includes one or more nucleic acids and equivalents thereof known to those skilled in the art, and so forth. The term "or" is not meant to be exclusive to one or the terms it designates. For example, as it is used in a phrase of the structure "A or B" may denote A alone, B alone, or both A and B.

Unless defined otherwise, all technical and scientific terms used herein have the same meanings as commonly understood by one of ordinary skill in the art to which this invention belongs. Although any methods and systems similar or equivalent to those described herein can be used in the practice or testing of the present invention, the methods, devices, and materials are now described. All publications mentioned herein are incorporated herein by reference for the purpose of describing and disclosing the processes, systems, and methodologies that are reported in the publications which might be used in connection with the invention. Nothing herein is to be construed as an admission that the invention is not entitled to antedate such disclosure by virtue of prior invention.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

What is claimed is:

1. A compound having the formula

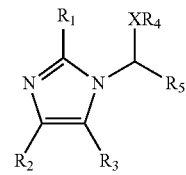

wherein
$R_1$ is selected from the group consisting of H, Br, $NO_2$, butyl, OMe, CN, methyl, carboxy, and methyl carboxylate;
$R_2$ is selected from the group consisting of H, $NO_2$, butyl, OMe, CN, histidine, and histamine;
$R_3$ is selected from the group consisting of H, $NO_2$, butyl, OMe, and CN, or one of
$R_2$ and $R_3$ is selected from the group consisting of Br, 2-aminoethyl, acetate, and N-(prop-2-ynyl)acetamide and one of $R_2$ and $R_3$ is H;
$XR_4$ is selected from the group consisting of $OCH_2CH_3$ and $OCH_3$;
$R_5$ is

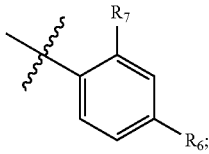

$R_6$ is selected from the group consisting of H, Br, $NO_2$, butyl, $COR_8$ and $COR_9$;

$R_7$ is selected from the group consisting of H, Br, OMe, CN, $NO_2$, $COR_8$, and $COR_9$;

$R_8$ is a hydroxyl-containing cancer therapeutic agent; and $R_9$ is an amine-containing cancer therapeutic agent, wherein one of $R_6$ and $R_7$ is $COR_8$ or $COR_9$.

2. The compound of claim 1, wherein $XR_4$ is OEt.

3. The compound of claim 1, wherein $R_1$, $R_2$, and $R_3$ are H.

4. The compound of claim 1, wherein said compound is insoluble at pH 7.4 and may be hydrolyzed at pH 5.5.

5. The compound of claim 1, wherein said compound hydrolyzes about 10 times faster at pH 5.5 than at pH 7.4.

6. The compound of claim 1, wherein $R_1$, $R_2$, and $R_3$ are H; $XR_4$ is $OCH_2CH_3$; and:
- (i) $R_6$ is $COR_8$ and $R_7$ is H;
- (ii) $R_6$ is $COR_9$ and $R_7$ is H;
- (iii) $R_6$ is H and $R_7$ is $COR_8$; or
- (iv) $R_6$ is H and $R_7$ is $COR_9$.

* * * * *